(12) United States Patent
Tischer et al.

(10) Patent No.: US 7,229,797 B1
(45) Date of Patent: Jun. 12, 2007

(54) ENZYMATIC SYNTHESIS OF DEOXYRIBONUCLEOSIDES

(75) Inventors: Wilhelm Tischer, Peissenberg (DE); Hans-Georg Ihlenfeldt, Iffeldorf (DE); Octavian Barzu, Antony (FR); Hiroshi Sakamoto, Meudon (FR); Elisabeth Pistotnik, Creteil (FR); Philippe Marlière, Etiolles (FR); Sylvie Pochet, Paris (FR)

(73) Assignee: Institut Pasteur, Paris (FR)

( * ) Notice: Subject to any disclaimer, the term of this patent is extended or adjusted under 35 U.S.C. 154(b) by 532 days.

(21) Appl. No.: 10/049,750

(22) PCT Filed: Aug. 18, 2000

(86) PCT No.: PCT/EP00/08088

§ 371 (c)(1),
(2), (4) Date: Dec. 9, 2002

(87) PCT Pub. No.: WO01/14566

PCT Pub. Date: Mar. 1, 2001

(30) Foreign Application Priority Data

Aug. 20, 1999 (EP) .................................. 99116425

(51) Int. Cl.
*C12P 19/40* (2006.01)
*C07K 14/00* (2006.01)
*C07H 21/04* (2006.01)
*C12P 19/38* (2006.01)
*C12P 21/06* (2006.01)
*C12N 9/10* (2006.01)
*C12N 9/12* (2006.01)
*C12N 9/88* (2006.01)

(52) U.S. Cl. .................. 435/88; 435/87; 435/69.1; 435/320.1; 435/193; 435/194; 435/232; 435/233; 530/350; 536/23.2

(58) Field of Classification Search ................... 435/87, 435/88, 69.1, 320.1, 193, 194, 233, 232; 530/350; 536/23.2
See application file for complete search history.

(56) References Cited

FOREIGN PATENT DOCUMENTS

| EP | 0 038 569 | 10/1981 |
| EP | 0 090 417 | 10/1983 |
| EP | 0 411 158 | 2/1991 |
| EP | 0593757 B1 * | 1/1997 |
| WO | WO 96/32491 * | 10/1997 |

OTHER PUBLICATIONS

Witkowski et al., Biochemistry 38:11643-11650, 1999.*
Seffernick et al., J. Bacteriol. 183(8):2405-2410, 2001.*
Branden et al., Introduction to Protein Structure, Garland Publishing Inc., New York, p. 247,1991.*
Barbas, C., Ph.D. Thesis,Texas A&M University, 1989.*
Tozzi et al., FEBS Journal 273:1089-1101, 2006.*
Bzowska et al., Pharmacology & Therapeutics 88:349-425, 2000.*
Pugmire et al., Biochem. J. 361:1-25, 2002.*
Patent Abstracts of Japan, vol. 007, No. 151, Jul. 1, 1983 & JP 58 063393—Apr. 15, 1983.
C.F. Barbas IIII, et al. "Overexpression and substrate . . . phosphorylase" Bioorganic Chemistry, vol. 19,—pp. 261-269, 1991.
M. Fischer, et al., "The cloning of the *Escherichia* . . . Operon", Gene, vol. 17, No. 3. pp. 291-298, 1982.
M. S. Hershfield, et al. "Use of site-directed . . . glycol:", Proc. Natl. Acad. Sci. vol. 88. (1991)), pp. 7185-7189.

* cited by examiner

*Primary Examiner*—Delia M. Ramirez
(74) *Attorney, Agent, or Firm*—Fulbright & Jaworski L.L.P.

(57) ABSTRACT

The present invention relates to a method for the in vitro enzymatic synthesis of deoxyribonucleosides and enzymes suitable for this method.

27 Claims, 4 Drawing Sheets

ENZYMATIC SYNTHESIS OF DEOXYRIBONUCLEOSIDES

DESCRIPTION

The present invention relates to a method for the in vitro enzymatic synthesis of deoxyribonucleosides and enzymes suitable for this method.

Natural deoxyribonucleosides (deoxyadenosine, dA; deoxyguanosine, dG; deoxycytidine, dC and thymidine, dT) are building blocks of DNA. The N-glycosidic bond between nucleobase and sugar involves the $N_1$ of a pyrimidine or the $N_9$ of a purine ring and the $C_1$ of deoxyribose.

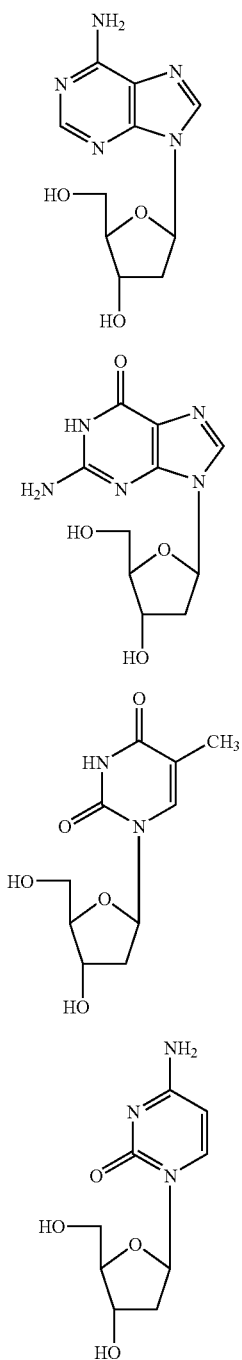

In the living cells, the four deoxyribonucleosides (dN) result from the "salvage pathway" of nucleotide metabolism. A group of enzymes is involved in cellular catabolism of deoxyribonucleosides. Besides deoxyriboaldolase (EC 4.1.2.4) and deoxyribomutase (EC 5.4.2.7), this group also includes thymidine phosphorylase (EC 2.4.2.4) and purine nucleoside phosphorylase (EC 2.4.2.1.). These four enzymes are induced by the addition of deoxyribonucleosides to the growth medium. The genes coding for these enzymes have been shown to map closely together on the bacterial chromosome (Hammer-Jesperson and Munch-Peterson, Eur. J. Biochem. 17 (1970), 397 and literature cited therein). In *E. coli* the genes as described above are located on the deo operon which exhibits an unusual and complicated pattern of regulation (Valentin-Hansen et al., EMBO J. 1(1982) 317).

Using the enzymes of the deo operon for synthesis of deoxynucleosides was described by C. F. Barbas III (Overproduction and Utilization of Enzymes in Synthetic Organic Chemistry, Ph.D. Thesis (1989), Texas A&M University). He applied phosphopentomutase and thymidine phosphorylase for the synthesis of deoxynucleosides. Deoxyribose 5-phosphate was prepared by chemical synthesis (Barbas III et al., J. Am. Chem. Soc. 112 (1990), 2013–2014), which makes this compound expensive as starting material and not suitable for large scale synthesis. He also made deoxyriboaldolase available as a recombinant enzyme and investigated its synthetic applicability but neither he nor C. -H. Wong (Microbial Aldolases in Carbohydrate Synthesis: ACS Symp. Ser. No. 466: Enzymes in Carbohydrate Synthesis, Eds. M. D. Bednarski, E. S. Simon (1991), 23–27) were able to carry out a coupled one-pot synthesis employing all three enzymes. It appears likely that some drawbacks exist which could not be circumvented. Among these drawbacks are insufficient chemical equilibrium, instability of intermediates, such as deoxyribose 1-phosphate and inactivation and inhibition effects of involved compounds on the enzymes.

Evidence of an advantageous equilibrium is given by S. Roy et al. (JACS 108 (1986), 1675–78). For the aldolase reaction the equilibrium is on the desired product side (deoxyribose 5-phosphate), for the phosphopentomutase it is on the wrong side (also deoxyribose 5-phosphate) and for the purine nucleoside phosphorylase it is on the desired synthesis product side. The authors suggest coupling of the three enzyme reactions to obtain reasonable yields. Contrary to these suggestions they prepared deuterated deoxyguanosine and thymidine in a two step procedure, that is deoxyribose 5-phosphate in a first step and deoxynucleoside in a second step. Isolated yields of the second step were 11% and 5% for deoxyguanosine and thymidine, respectively. These low yields are also obtained in the preparation of arabinose-based nucleosides (Barbas III (1990), supra). These low yields indicate serious drawbacks for the use of the enzymes of the deo operon in a synthetic route which have to work in the reverse direction of their biological function, which is degradation of deoxynucleosides.

Thus, there does not exist any economical commercial method at present for the enzymatic in vitro synthesis of deoxyribonucleosides. Hitherto, for commercial purposes, deoxynucleosides are generated from fish sperm by enzymatic cleavage of DNA. This method, however, involves several disadvantages, particularly regarding difficulties of obtaining the starting material in sufficient quantity and quality.

Therefore, it was an object of the invention to provide a method, by means of which the drawbacks of the prior are eliminated at least partially and which allows efficient and economical synthesis of deoxyribonucleosides without any dependence on unreliable natural sources.

Surprisingly, it was found that the drawbacks of previous enzymatic synthesis routes can be avoided and deoxyribonucleosides can be obtained in high yields of e.g. at least 80% based on the amount of starting material.

In a first aspect, the present invention relates to a method for the in vitro enzymatic synthesis of deoxyribonucleosides comprising reacting deoxyribose 1-phosphate (dR1P) and a nucleobase, wherein a deoxyribonucleoside and inorganic phosphate are formed.

The reaction is catalyzed by an enzyme which is capable of transferring a deoxyribose moiety to a nucleobase, with a deoxyribonucleoside being formed. Preferably, the reaction is catalyzed by a thymidine phosphorylase (TP, EC 2.4.2.4) or a purine nucleoside phosphorylase (PNP, EC 2.4.2.1). For the EC designation of these enzymes and other enzymes mentioned below reference is made to the standard volume Enzyme Nomenclature 1992, Ed. E. C. Webb, Academic Press, Inc.

These enzymes and other enzymes mentioned below are obtainable as native proteins from natural sources, i.e. any suitable organism selected from eukaryotes, prokaryotes and archaea including thermophilic organisms. Further, these enzymes are obtainable as recombinant proteins from any suitable host cell which is transformed or transfected with a DNA encoding said enzyme. The host cell may be a eukaryotic cell, a prokaryotic cell or an archaea cell. Particular preferred sources of native or recombinant TP or PNP are prokaryotic organisms such as *E. coli*. Recombinant TP may be isolated from *E. coli* strain pHSP 282 (CNCM I-2186) deposited on Apr. 23, 1999, which is a recombinant *E. coli* strain transformed with a plasmid containing the *E. coli* deoA (thymidine phosphorylase) insert. Recombinant PNP may be isolated from *E. coli* strain pHSP 283 (CNCM I-2187) deposited on Apr. 23, 1999, which is a recombinant *E. coli* strain transformed with a plasmid containing the *E. coli* deoD (purine nucleoside phosphorylase) insert. The nucleotide sequence of the TP gene and the corresponding amino acid sequence are shown in SEQ ID NO. 1 and 2. The nucleotide sequence of the PNP gene and the corresponding amino acid sequence are shown in SEQ ID NO. 15 and 16 and 3 and 4.

The nucleobase, to which the deoxyribose unit is transferred, will be selected from any suitable nucleobase. For example, the nucleobase may be a naturally occurring nucleobase such as thymine, uracil, adenine, guanine or hypoxanthine. It should be noted, however, that also non-naturally occurring analogs thereof are suitable as enzyme substrates such as 2-thio-uracil, 6-aza-uracil, 5-carboxy-2-thiouracil, 6-aza-thymine, 6-aza-2-thio-thymine and 2,6-diamino-purine.

Preferably the inorganic phosphate is removed from the reaction. This removal is preferably effected by (i) conversion to inorganic pyrophosphate, (ii) precipitation/complexation and/or (iii) substrate phosphorylation.

Conversion to inorganic pyrophosphate may be effected by a phosphate transfer from a phosphorylated, preferably polyphosphorylated substrate such as fructose diphosphate (FDP), wherein a phosphate group is cleaved from the phosphorylated substrate and reacts with the inorganic phosphate, with inorganic pyrophosphate (PPi) being formed. This phosphate transfer is preferably catalyzed by a PPi-dependent phosphorylase/kinase, e.g. by a PPi-dependent phosphofructokinase (PPK-PPi, EC 2.7.1.90), which catalyzes the reaction of fructose diphosphate (FDP) and inorganic phosphate to fructose 6-phosphate (F6P) and inorganic pyrophosphate. Preferred sources of PPi-dependent kinases/phosphorylases and genes coding therefor are from *Propionibacterium freudenreichii* (*shermanii*) or from potato tubers.

Further, the inorganic phosphate may be removed from the reaction by precipitation and/or complexation which may be effected by adding polyvalent metal ions, such as calcium or ferric ions capable of precipitating phosphate or by adding a complex-forming compound capable of complexing phosphate. It should be noted that also a combination of pyrophosphate formation and complexation/precipitation may be carried out.

Furthermore, the removal of inorganic phosphate may be effected by substrate phosphorylation. Thereby the inorganic phosphate is transferred to a suitable substrate, with a phosphorylated substrate being formed. The substrate is preferably selected from saccharides, e.g. disaccharides such as sucrose or maltose. When using disaccharides as substrate, a monosaccharide and a phosphorylated monosaccharide are obtained. The phosphate transfer is catalyzed by a suitable phosphorylase/kinase such as sucrose phosphorylase (EC 2.4.1.7) or maltose phosphorylase (EC 2.4.1.8). Preferred sources of these enzymes are *Leuconostoc mesenteroides*, *Pseudomonas saccherophila* (sucrose phosphorylase) and *Lactobacillus brevis* (maltose phosphorylase).

The phosphorylated substrate may be further reacted by additional coupled enzymatic reactions, e.g. into a galactoside (Ichikawa et al., Tetrahedron Lett. 36 (1995), 8731–8732). Further, it should be noted that phosphate removal by substrate phosphorylation may also be coupled with other phosphate removal methods as described above.

Deoxyribose 1-phosphate (dR1P), the starting compond of the method of the invention, is a rather unstable compound, the isolation of which is difficult. In a preferred embodiment of the present invention, d1RP is generated in situ from deoxyribose 5-phosphate (dR5P) which is relatively stable at room temperature and neutral pH. This reaction is catalyzed by a suitable enzyme, e.g. a deoxyribomutase (EC 5.4.2.7) or a phosphopentose mutase (PPM, EC 5.4.2.7) which may be obtained from any suitable source as outlined above. The reaction is preferably carried out in the presence of divalent metal cations, e.g. $Mn^{2+}$ or $Co^{2+}$ as activators. Preferred sources of deoxyribomutase are enterobacteria. Particular preferred sources of native or recombinant PPM are prokaryotic organisms such as *E. coli*. Recombinant PPM may be isolated from *E. coli* strain pHSP 275 (CNCM I-2188) deposited on Apr. 23, 1999, which is a recombinant *E. coli* strain transformed with a plasmid containing the *E. coli* deo B (phosphopentose mutase) insert. The nucleotide sequence of the PPM gene and the corresponding amino acid sequence are shown in SEQ ID NO. 17 and 18 and 5 and 6.

dR5P may be generated by a condensation of glyceraldehyde 3-phosphate (GAP) with acetaldehyde. This reaction is catalyzed by a suitable enzyme, preferably by a phosphopentose aldolase (PPA, EC 4.1.2.4). The reaction exhibits an equilibrium constant favorable to the formation of the phosphorylated sugar ($K_{eq}$=[dR5P]/[acetaldehyde]×[GAP]=4.2× $10^3 \times M^{-1}$). PPA forms an unstable Schiff base intermediate by interacting with the aldehyde. Particular preferred sources of native or recombinant PPA are prokaryotic organisms such as *E. coli*. Recombinant PPA may be isolated from *E. coli* strain pHSP 276 (CNCM I-2189) deposited on Apr. 23, 1999. This recombinant *E. coli* strain is transformed with a plasmid containing the deoC (phosphopentosealdolase)

insert. The nucleotide sequence of the PPA gene and the corresponding amino acid sequence are shown in SEQ ID NO. 19 and 20 and 7 and 8.

GAP is a highly unstable compound and, thus, should be generated in situ from suitable precursors which are preferably selected from fructose 1,6-diphosphate(FDP), dihydroxyacetone (DHA) and/or glycerolphosphate (GP), with FDP being preferred.

FDP can be converted by an FDP aldolase (EC 4.1.2.13) selected from FDP aldolases I and FDP aldolases II to GAP and dihydroxyacetone phosphate ($K_{eq}$=[FDP]/[GAP]× [DHAP]=$10^4 M^{-1}$). The two families of FDP aldolases giving identical end products (GAP and DHAP) via two chemically distinct pathways may be used for this reaction. FDP aldolase I forms Schiff base intermediates like PPA, and FDP aldolase II which uses metals ($Zn^{2+}$) covalently bound to the active sites to generate the end products. FDP-aldolase I is characteristic to eukaryotes, although it is found in various bacteria. FDP-aldolase II is more frequently encountered in prokaryotic organisms. If FDP-aldolase reacts with FDP in the presence of acetaldehyde, the latter compound can interact with DHAP to yield an undesired condensation by-product named deoxyxylolose 1-phosphate (dX1P). Thus, the reaction is preferably conducted in a manner by which the generation of undesired side products is reduced or completely suppressed.

Particular preferred sources of native or recombinant FDP aldolases are prokaryotic or eukaryotic organisms. For example, FDP aldolase may be isolated from rabbit muscle. Further, FDP aldolase may be obtained from bacteria such as *E. coli*. Recombinant FDP aldolase may be isolated from recombinant *E. coli* strain pHSP 284 (CNCM I-2190) which is transformed with a plasmid containing the *E. coli* fba (fructose diphosphate aldolase) insert. The nucleotide sequence of the *E. coli* FDP aldolase gene and the corresponding amino acid sequence are shown in SEQ ID NO. 9 and 10.

On the other hand, GAP may be generated from DHAP and ATP, with dihydroxyacetone phosphate (DHAP) and ADP being formed and subsequent isomerization of DHAP to GAP in a reaction catalyzed by a glycerokinase (GK, EC 2.7.1.30) and a triose phosphate isomerase (TIM, EC 5.3.1.1). Suitable glycerokinases are obtainable from *E. coli*, suitable triose phosphate isomerases are obtainable from bovine or porcine muscle.

In a still further embodiment of the present invention GAP may be generated from glycerol phosphate (GP) and $O_2$, with DHAP and $H_2O_2$ being formed and subsequent isomerization of DHAP to GAP in a reaction catalyzed by a glycerophosphate oxidase (GPO, EC 1.1.3.21) and a triose phosphate isomerase (TIM, EC 5.3.1.1). Suitable glycerophosphate oxidases are obtainable from *Aerococcus viridans*.

In an alternative embodiment of the present invention deoxyribose 5-phosphate (dR5P) is generated by phosphorylation of deoxyribose. Preferably this reaction is carried out in the presence of a suitable enzyme, e.g. a deoxyribokinase (dRK, EC 2.7.1.5) which may be obtained from prokaryotic organisms, particularly *Salmonella typhi* and in the presence of ATP. The nucleotide sequence of the *Salmonella* dRK gene and the corresponding amino acid sequence are shown in SEQ ID NO. 11 and 12.

By the reaction as outlined above deoxyribonucleosides are obtained which contain a nucleobase which is accepted by the enzymes TP and/or PNP. TP is specific for thymidine (T), uracil (U) and other related pyrimidine compounds. PNP uses adenine, guanine, hypoxanthine or other purine analogs as substrates.

The synthesis of deoxyribonucleosides which are not obtainable by direct condensation such as deoxycytosine (dC), thus, require an additional enzymatic reaction, wherein a deoxyribonucleoside containing a first nucleobase is reacted with a second nucleobase, with a second ribonucleoside containing the second nucleobase being formed. The second nucleobase is preferably selected from cytosine and analogs thereof such as 5-azacytosine. It should be noted, however, that also other nucleobases such as 6-methyl purine, 2-amino-6-methylmercaptopurine, 6-dimethylaminopurine, 2,6-dichloropurine, 6-chloroguanine, 6-chloropurine, 6-azathymine, 5-fluorouracil, ethyl-4-amino-5-imidazole carboxylate, imidazole-4-carboxamide and 1,2,4-triazole-3-carboxamide may be converted to the corresponding deoxyribonucleoside by this nucleobase exchange reaction (Beaussire and Pochet, Nucleosides & Nucleotides 14 (1995), 805–808, Pochet et al., Bioorg. Med. Chem. Lett. 5 (1995), 1679–1684, Pochet and Duqué, Nucleosides & Nucleotides 17 (1998), 2003–2009, Pistotnik et al., Anal. Biochem. 271 (1999), 192–199). This reaction is preferably catalyzed by an enzyme called nucleoside 2-deoxyribosyltransferase (NdT, EC 2.4.2.6) which transfers the glycosyl moiety from a first deoxynucleoside to a second nucleobase, e.g. cytosine. A preferred source of native or recombinant NdT are prokaryotic organisms such as *lactobacilli*, particularly *Lactobacillus leichmannii*. Recombinant NdT may be isolated from recombinant *E. coli* strain pHSP 292 (CNCM I-2191) deposited on Apr. 23, 1999, which is transformed with a plasmid containing the *L. leichmannii* NdT (nucleoside 2-deoxyribosyltransferase) insert. The nucleotide sequence of the NdT gene and the corresponding amino acid sequence are shown in SEQ ID NO. 13 and 14.

A further aspect of the present invention is a method for the in vitro enzymatic synthesis of deoxyribonucleosides comprising the steps of: (i) condensing glyceraldehyde 3-phosphate (GAP) with acetaldehyde to deoxyribose 5-phosphate (dR5P), (ii) isomerizing deoxyribose 5-phosphate to deoxyribose 1-phosphate (dR1P) and (iii) reacting deoxyribose 1-phosphate and a nucleobase, wherein a deoxyribonucleoside and inorganic phosphate are formed. Preferably, the reaction is carried out without isolating intermediate products and, more preferably, as a one-pot reaction. Further, the removal of the inorganic phosphate from the reaction is preferred.

As outlined above, the glyceraldehyde 3-phosphate may be generated from PDP, DHA and/or GP. Preferably, FDP is used as a starting material.

In order to avoid the production of undesired by-products and the toxic effects of acetaldehyde, the course of the reaction is preferably controlled by suitable means. Thus, preferably, the reaction is carried out in a manner such that the acetaldehyde concentration in step (ii) is comparatively low, e.g. less than 100 mM, particularly less than 50 mM, e.g. by adding the acetaldehyde in portions or continuously during the course of the reaction and/or by removing excess acetaldehyde. Further, it is preferred that before step (ii) excess starting materials and/or by-products, particularly fructose 1,6-diphosphate and/or deoxyxylulose 1-phosphate (dX1P), are removed. This removal may be effected by chemical and/or enzymatic methods, e.g. precipitating FDP with ferric salts or enzymatically degrading X1P via dihydroxyacetone phosphate. Alternatively or additionally the reaction conditions may be adjusted such that before step (ii) no substantial amounts, preferably less than 10 mM, of starting materials and/or by-products, particularly fructose 1,6-diphosphate and/or deoxyxylulose 1-phosphate, are present in the reaction mixture.

In still another embodiment, the present invention relates to a method for the in vitro enzymatic synthesis of deoxyribonucleosides comprising the steps of: (i) phosphorylating deoxyribose to deoxyribose 5-phosphate, (ii) isomerizing deoxyribose 5-phosphate to deoxyribose 1-phosphate and (iii) reacting deoxyribose 1-phosphate and nucleobase, wherein a deoxyribonucleoside and inorganic phosphate are formed. Preferably, these reactions are carried out with isolating intermediate products and, more preferably, as a one-pot reaction. To obtain a better yield the removal of inorganic phosphate from step (iii) is preferred.

By the process as described above naturally occurring deoxyribonucleosides such as dA, dG, dT, dU and dT but also analogs thereof containing non-naturally occurring nucleobases and/or non-naturally occurring deoxyribose sugars such as 2'-deoxy-3'-azido-deoxyribose or 2'-deoxy-4'-thio-deoxyribose may be produced.

The deoxyribonucleosides obtained may be converted to further products according to known methods. These further reaction steps may comprise the synthesis of deoxyribonucleoside mono-, di- or triphosphates, of H-phosphonates or phosphoramidites. Additionally or alternatively, labelling groups such as radioactive or chemical labelling groups may be introduced into the deoxyribonucleosides.

Still a further aspect of the present invention is the use of an isolated nucleic acid molecule encoding a nucleoside 2-deoxyribosyl transferase (NdT, EC 2.4.2.6) for the preparation of an enzyme in an in vitro enzymatic synthesis process, wherein a deoxyribonucleoside containing a first nucleobase is reacted with a second nucleobase, with a deoxyribonucleoside containing the second nucleobase being formed. The second nucleobase is preferably selected from cytidine and analogs thereof, 2,6-dichloro-purine, 6-chloro-guanine, 6-chloro-purine, 6-aza-thymine and 5-fluoro-uracil. The first nucleobase is preferably selected from thymine, guanine, adenine or uracil.

More preferably, the nucleic acid molecule encoding an NdT comprises (a) the nucleotide sequence shown in SEQ ID NO. 13 or its complementary sequence, (b) a nucleotide sequence corresponding to the sequence of (a) in the scope of degeneracy of the genetic code or (c) the nucleotide sequence hybridizing under stringent conditions to the sequence (a) and/or (b). Apart from the sequence of SEQ ID NO. 13 the present invention also covers nucleotide sequences coding for the same polypeptide, i.e. they correspond to the sequence within the scope of degeneracy of the genetic code, and nucleotide sequence hybridizing with one of the above-mentioned sequences under stringent conditions. These nucleotide sequences are obtainable from SEQ ID NO. 13 by recombinant DNA and mutagenesis techniques or from natural sources, e.g. from other *Lactobacillus* strains.

Stringent hybridization conditions in the sense of the present invention are defined as those described by Sambrook et al., Molecular Cloning, A Laboratory Manual, Cold Spring harbor laboratory Press (1989), 1.101–1.104. According to this, hybridization under stringent conditions means that a positive hybridization signal is still observed after washing for one hour with 1×SSC buffer and 0.1% SDS at 55° C., preferably at 62° C. and most preferred at 68° C., in particular, for one hour in 0.2×SSC buffer and 0.1% SDS at 55° C., preferably at 62° C. and most preferred at 68° C.

Moreover, the present invention also covers nucleotide sequences which, on nucleotide level, has an identity of at least 70%, particularly preferred at least 80% and most preferred at least 90% to the nucleotide sequence shown in SEQ ID NO. 13. Percent identity are determined according to the following equation:

$$I = \frac{n}{L} \times 100$$

wherein 1 arc percent identity, L is the length of the basic sequence and n is the number of nucleotides or amino acids matches between the selected sequence and that of the basic sequence.

Still another subject matter of the present invention is a recombinant vector comprising at least one copy of the nucleic acid molecule as defined above, operatively linked with an expression control sequence. The vector may be any prokaryotic or eukaryotic vector. Examples of prokaryotic vectors are chromosomal vectors such as bacteriophages (e.g. bacteriophage Lambda) and extrachromosomal vectors such as plasmids (see, for example, Sambrook et al., supra, Chapter 1–4). The vector may also be a eukaryotic vector, e.g. a yeast vector or a vector suitable for higher cells, e.g. a plasmaid vector, viral vector or plant vector. Suitable eukaryotic vectors are described, for example, by Sambrook et al., supra, Chapter 16. The invention moreover relates to a recombinant cell transformed with the nucleic acid or the recombinant vector as described above. The cell may be any cell, e.g. a prokaryotic or eukaryotic cell. Prokaryotic cells, in particular, *E. coli* cells, are especially preferred.

The invention refers to an isolated polypeptide having NdT activity encoded by the above-described nucleic acid and its use for the preparation of deoxyribonucleoside. Preferably, the polypeptide has the amino acid sequence shown in SEQ ID NO. 14 or an amino acid sequence which is at least 70%, particularly preferred at least 80% and most preferred at least 90% identical thereto, wherein the identity may be determined as described above.

Finally, the present invention also relates to the use of isolated nuclecic acid molecules having thymidine phosphorylase (TP), purine nucleside phosphorylase (PNP), phosphopentose mutase (PPM), phosphopentose aldolase (PPA), FDP aldolase and deoxyribokinase (dRK) activity for the preparation of an enzyme for a method for the in vitro synthesis of deoxynucleosides. Preferably, these nucleic acids are selected (a) from a nucleotide sequence shown in SEQ ID NO. 1, 3, 5, 7, 9 or 11 or their complementary sequences, (b) a nucleotide sequence corresponding to a sequence of (a) within the scope of degeneracy of the genetic code or (c) a nucleotide sequence hybridizing under stringent conditions to a sequence (a) and/or (b).

Isolated polypeptides having TP, PNP, PPM, PPA, FDP aldolase or dRK activity encoded by the above-described nucleic acids may be used for the preparation of deoxyribonucleosides. Preferably, these polypeptides have the amino acid sequence shown in SEQ ID NO. 2, 4, 16, 6, 18, 8, 20, 10 or 12 or an amino acid sequence which is at least 70%, particularly preferred at least 80% and most preferred at least 90% identical thereto, wherein the identity may be determined as described above.

An isolated nucleic acid molecule encoding a dRK may be used for the preparation of an enzyme for an in vitro method for the enzymatic synthesis of deoxyribonucleosides comprising the step of phosphorylating deoxyribose to deoxyribose 5-phosphate, wherein said nucleic acid molecule comprises (a) the nucleotide sequence shown in SEQ ID NO. 11 or its complementary sequence, (b) a nucleotide sequence corresponding to the sequence of (a) in the scope of the degeneracy of the genetic code or (c) a nucleotide sequence hybridizing under stringent conditions to the sequence of (a) and/or (b). Correspondingly, an isolated polypeptide having dRK activity is suitable for an in vitro method for the enzymatic synthesis of deoxyribonucleosides as outlined above.

The *E. coli* strains pHSP 282 (CNCM I-2186), pHSP 283 (CNCM I-2187), pHSP 275 (CNCM I-2188), pHSP 276 (CNCM 2189), pHSP 284 (CNCM I-2190) and pHSP 292 (CNCM I-2191) were deposited according to the regulations of the Budapest Treaty on Apr. 23, 1999 at the Collection Nationale de Culture de Microorganismes, Institut Pasteur, 25, Rue de Docteur Roux, 75724 Paris Cedex 15.

Example 1

Sources of Enzymes

Figure 1:
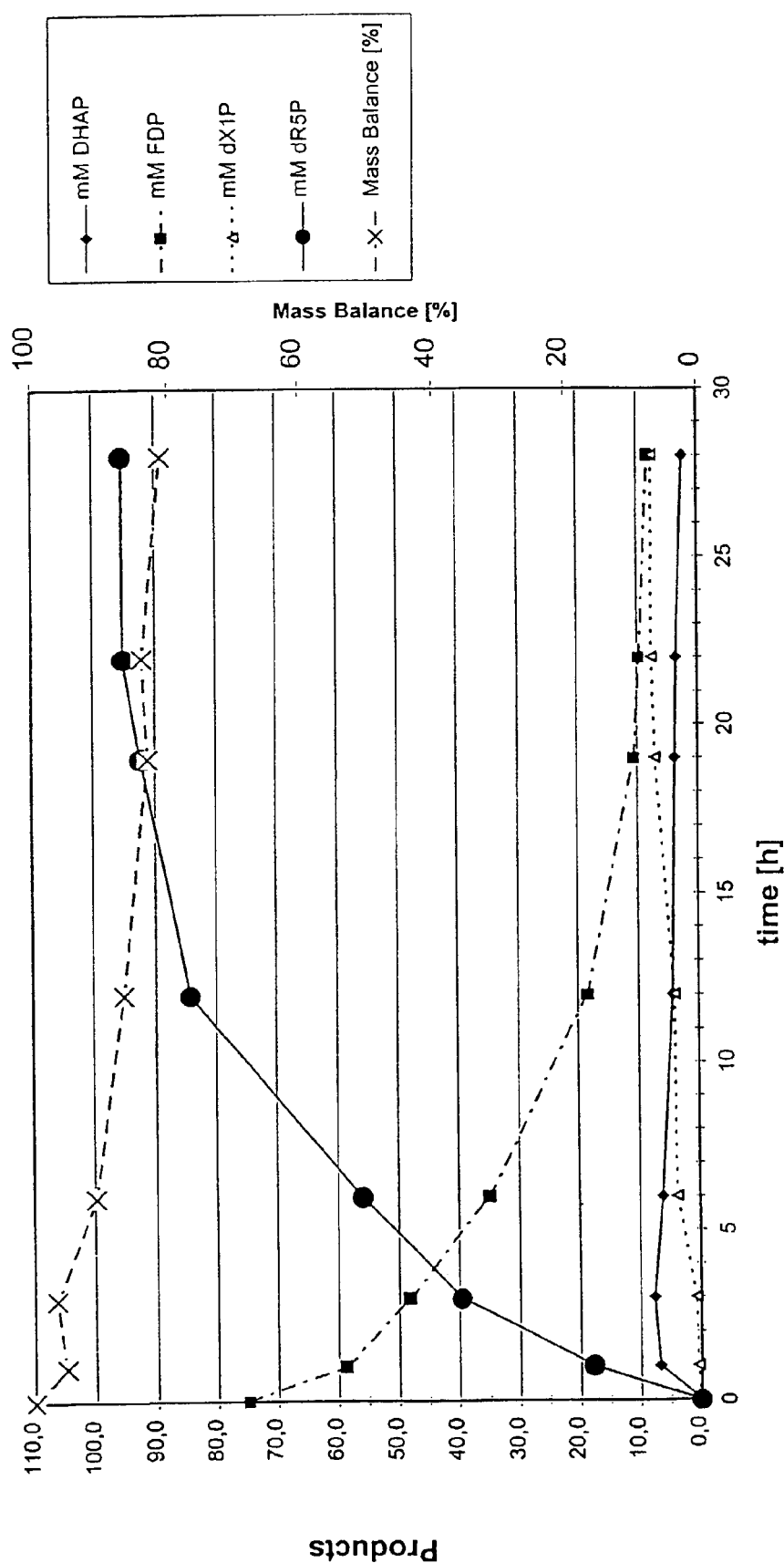
FIG. 1 shows the synthesis of dR5P according to Example 12.

L-glycerol 3-phosphate oxidase (1.1.3.21) from *Aerococcus viridans*, sucrose phosphorylase (2.4.1.7), fructose 6-phosphate kinase (2.7.1.90) from *Propionibacterium freudenreichii*, rabbit muscle aldolase (RAMA), formate dehydrogenase, glycerolphosphate dehydrogenase (GDH), triosephosphate isomerase (TIM), catalase, glycerol 3-phosphate oxidase and maltose phosphorylase were obtained from commercial sources (Roche Diagnostics, Sigma) or as described in the literature.

FDP aldolase II (4.1.2.13), phosphopentose aldolase (PPA, EC 4.1.2.4), phosphopentose mutase (PPM, EC 5.4.2.7), thymidine phosphorylase (TP, EC 2.4.2.4), purine nucleoside phosphorylase (PNP, EC 2.4.2.1), nucleoside 2-deoxyribosyl transferase (NdT, EC 2.4.2.6) were obtained from *E. coli* strains deposited at CNCM (see above).

Example 2

Protocol of the synthesis of deoxyadenosine

Reaction mixture A was prepared by adding acetaldehyde (final concentration 250 mM), FDP aldolase II (0.5 U/ml), PPA (2.5 U/ml) to 20 ml of 100 mM fructose-1,6-diphosphate (FDP), pH 7.6 and incubating overnight at 4° C.

Mixture B was prepared by adding MnCl$_2$ (final concentration 0.6 mM), glucose 1.6-diphosphate (15 μM), PPM (1.5 U/ml), PNP (0.4 U/ml), SP (1.5 U/ml) pentosephosphate aldolase, PPA (2 U/ml) and FDP aldolase II (0.5 U/ml) to 10 ml 0.9 M sucrose, pH 7.6, at room temperature.

2 ml of A were added over B at a temperature of 20° C. After 1 hour 2.5 ml were added. After another hour 3.0 ml A were added. After another 1.5 h 3.5 ml A were added. After another 1.5 h 4 ml A were added and after another 1–1.5 h 5 ml A were added and left to stand overnight.

At each time of addition of A the amounts of FDP, dR5P, dX1P and dA in the reaction mixture were determined and the yield was calculated. The concentration of acetaldehyde was kept between 20–30 mM. The results are shown in Table 1:

TABLE 1

| Time | Volume | Concentrations (mM) | | | Yield (mmol) |
|---|---|---|---|---|---|
| (h) | (ml) | dR5P | dA | dX1P | dA |
| 0 | 12 | 4 | 0 | 1.2 | 0 |
| 1 | 12 | 3.4 | 3.2 | 1 | 0.04 |
| 2 | 14.5 | 7.9 | 8.0 | 2.6 | 0.12 |
| 3.5 | 17.5 | 13 | 16.2 | 4.3 | 0.28 |
| 5 | 21 | 11.7 | 21.7 | | 0.46 |
| 6 | 25 | | 23.7 | | 0.59 |
| 22 | 30 | 11 | 40.4 | 13.2 | 1.21 |
| 30 | 30 | | 50.3 | | 1.51 |
| 54 | 30 | 8.9 | 60.6 | | 1.82 |

The starting amount of FDP was 1.92 mmol. The amount after completion of reaction was 0.150 mmol. Thus, 1.77 mmol were consumed, theoretically corresponding to 3.54 mmol equivalents dA. The amount of dA formed was 1.82 mmol, leading to a yield of 51.4% based on the amount of FDP.

Example 3

Removal of excess FDP by means of FeCl$_3$ 1.4 g (2.55 mmol) trisodium-fructose-1,6-disphosphate-octahydrate and 430 μl (335 mg, 7.6 mmol) acetaldehyde were dissolved in 15 ml of water at 4° C. A pH of 7.9 was adjusted by means of sodium hydroxide solution. 150 U pentosephosphate aldolase (PPA) were added, and code water (4° C.) was added to give 20 ml. After addition of 50 U *E. coli* aldolase II the mixture was stored at 4° C. After 2 h another 75 U PPA and 50 μl acetaldehyde (390 mg, 8.9 mmol) were added. After 20 h 500 U triosephosphate isomerase (TIM) were added. After 120 h the solution contained about 68 mM FDP, about 12 mM dX1P and about 45 mM dR5P. The reaction was stopped by adding 900 μl of a 2 M solution of iron(III) chloride in 0.01 M hydrochloric acid. The precipitate was centrifuged and washed, the resulting solution contained about 4 mM dX1P, about 9 mM FDP and about 25 mM dR5P.

Example 4

Removal of excess FDP and dX1P by degradation via DHAP 576 mg (1.05 mmol) trisodium-fructose-1,6-disphosphate-octahydrate were dissolved in 8 ml water, and the pH was adjusted at 8.1 by means of sodium hydroxide solution. 75 U PPA and 27 U rabbit muscle aldolase (RAMA) were added, and water was added to give 10 ml. 570 μl (440 mg, 10 mmol) acetaldehyde were added. The reaction was stored at 4° C. After 100 h the solution contained about 110 mM dX1P, about 5 mM FDP and about 85 mM dR5P (about 870 μmol). The reaction was stopped by adding hydrochloric acid until a pH of 2 was reached. After adding sodium hydroxide solution to give a pH of 5.5 the solution was stored.

For removing dX1P the acetaldehyde was evaporated and the solution was diluted with water to reach 30 ml. It was mixed with 3 ml 2.65 M sodium formate solution (8 mmol), and sodium hydroxide solution was added until a pH of 7.4 was reached. 23 U formate dehydrogenase (FDH), 6 mg NADH, 16 U RAMA and 20 U glycerolphosphate dehydrogenase (GDH) were added.

After 24 h at room temperature the concentrations of dX1P and FDP are below 3 mM, the loss of dR5P is less than 10%.

Example 5

Preparation of dR5P via G3P 1.1 g (2.0 mmol) trisodium-fructose-1,6-disphosphate-octahydrate were dissolved in 8 ml water. 1.58 mol of a 2.65 M sodium formate solution (4.2 mmol) and 14.2 mg NADH were added. A pH of 7.0 was adjusted by means of NaOH. After addition of 36 U RAMA, 50 U triosephosphate isomerase (TIM), 34 U GDH and 35 U FDH water was added to give 12 ml.

After incubation of 40 h at room temperature the FDP content was below 3 mM. The enzymes were denatured by acidification with hydrochloric acid to reach a pH of 2. Subsequently, the pH of the solution was adjusted at 4 and the solids were centrifuged and filtered off, respectively. Through dilution during purification a total volume of 25 ml was reached which contained about 160 mM of glycerol-3-phosphate (G3P).

4 ml of this solution (about 640 µmol G3P) were adjusted at a pH of 7.8 by means of sodium hydroxide solution. 7.8 kU catalase, 500 U TIM and 13 U glycerol 3-phosphate oxidase are added. The mixture was stirred very slowly in an open flask. After 30 min 18 U PPA were added. Acetaldehyde was added in portions of 30 µl (23.5 mg, 530 µmol) after 30, 60, 120, 180 and 240 min. After 24 h another 15 U PPA, 2.5 kU TIM and 100 µl (78 mg, 1.8 mmol) acetaldehyde were added. After 30 h the batch is sealed after addition of another 100 µl acetaldehyde. After a total of 45 h a concentration of about 60 mM dR5P was achieved and the reaction is completed. For preparing 2'-deoxyadenosine (e.g. Example 7) excess acetaldehyde must be distilled off.

Example 6

Preparation of a dR5P solution containing small amounts of dX1P or FDP

A solution of 60 mmol/l FDP and 120 mmol/l acetaldehyde having pH 7.4 was kept at a temperature of 15° C. 5 ml thereof were mixed with 4 U aldolase II, 2 U TIM and 40 U PPA and kept at 15° C. After 4, 8.5, 16.5 and 24 h 12 U PPA and 100 µl of a 34 vol. % solution of acetaldehyde in water (26.4 mg, 600 µmol) were added each. After 40 h the solution was allowed to reach room temperature. After 90 h the reaction solution had reached concentrations of about 3 mM FDP, about 4 mM dX1P and at least 70 mM dR5P. For stopping the reaction and removing acetaldehyde about 20% of the volume were distilled off.

Example 7

Preparation of deoxyadenosine (dA) from dR5P by means of barium acetate dR5P was used in the form of a solution prepared according to Examples 3–6. For instance, 10 ml of a solution of Example 6 diluted to have 70 mM dR5P (700 µmol dR5P) were mixed with 40 mg (300 µmol) adenine, 41 µg (50 nmol) tetracyclohexylammonium-glucose-1,6-disphosphate, 396 µg (2 µmol) manganese-II-acetate-tetrahydrate, 10 U pentosephosphate mutase (PPM) and 30 U purine-nucleoside phosphorylase (PNP). After 3 h another 27 mg (200 µmol) adenine and 26 mg (100 µmol) barium acetate were added. A further amount of 26 mg barium acetate was added after 4 h, one of 40 mg adenine after 7 h. After 10 h the reaction was completed. The solution had a concentration of 45 mM dA.

Example 8

Preparation of deoxyadenosine (dA) from dR5P by means of sucrose phosphorylase 10 ml of a solution of Example 6 diluted to 55 mM dR5P (550 µmol dR5P) were mixed with 81 mg (600 µmol) adenine, 41 µg (50 nmol) tetracyclohexylammonium-glucose-1,6-disphosphate, 396 µg (2 µmol) manganese-II-acetate-tetrahydrate, 10 U pentosephosphate mutase (PPM) 15 U purine nucleoside phosphorylase (PNP), 25 U sucrose phosphorylase and 340 mg (1 mmol) cane sugar.

After 3 h at room temperature the reaction was completed. The solution had a concentration of about 50 mM dA.

Example 9

Preparation of deoxyadenosine (dA) from dR5P by means of maltose phosphorylase 10 ml of a solution of dR5P diluted to 55 mM were mixed at pH 7.0 with 81 mg (600 µmol) adenine, 41 µg (50 nmoles) glucose 1,6-diphosphate, 396 µg (2 µmoles) manganese II-acetate tetrahydrate, 5 units pentose phosphate mutase (PPM), 10 units purine nucleoside phosphorylase, (PNP), 20 units maltose phosphorylase and 1080 mg (3 mmoles) maltose.

After 12 h at room temperature the reaction was completed. The solution had a concentration of 49 mM dA.

Example 10

Preparation of deoxycytosine (dC) from dR5P by means of sucrose phosphorylase 20 ml of a solution of dR5P diluted to 70 mM were mixed at pH 7.0 with 5.4 mg adenine (0.04 mmoles), 155 mg cytosine (1.4 mmoles), 82 µg (100 nmoles) glucose 1,6-diphosphate, 792 µg (4 µmoles) manganese II-acetate-tetrahydrate, 20 units PPM, 30 units PNP, 50 units 2-deoxyribosyl transferase (NdT), 50 units sucrose phosphorylase and 2.05 g (6 mmoles) sucrose.

After 18 h at 30° C. the solution had a concentration of 62 mM dC.

Example 11

Preparation of deoxyguanosine (dG) from dR5P by means of sucrose phosphorylase 20 ml of a solution of dR5P diluted to 70 mM were mixed at pH 7.0 with 91 mg guanine (0.6 mmoles), 82 µg (100 nmoles) glucose 1,6-diphosphate, 792 µg (4 µmoles) manganese II-acetate-tetrahydrate, 20 units PPM, 10 units PNP, 20 units sucrose phosphorylase and 2.05 g (6 mmoles) sucrose.

After 18 h at 37° C. the dG formed corresponds to 0.5 mmoles.

Example 12

Two step procedure of dA synthesis

In the first step dR5P was prepared by adding FDP-Aldolase II (AldII) from *E. coli*, pentosephosphate aldolase (PPA) from *E. coli* and triosephosphate isomerase (TIM) from *E. coli* to fructose-1,6-bisphosphate (FDP) and acetaldehyde (AcAld) essentially according to Ex. 6. FDP trisodium salt was mixed in a final concentration of 75 mM with AcAld (100 mM final concentration). The pH was adjusted to 7,4 by addition of sodium hydroxide. The reaction was started by adding PPA (12 kU/l), Ald II (0,3 kU/l) and TIM (2,5 kU/l). At 4 h 117 mM AcAld, at 7 h 117 mm AcAld, PPA 6 kU/l, TIM 2,5 kU/l and at 12 h 117 mM AcAld were added. The reaction was run at 21° C. Conversion was monitored by enzymatical assay using step by step glycerol-3-phosphate dehydrogenase (GDH), rabbit muscle aldolase (RAMA), triosephosphate isomerase (TIM), pentosephosphate aldolase (PPA) in the presence of NADH (0,26 mM in 300 mM triethanol amine buffer pH 7.6). Conversion is shown in FIG. 1.

Figure 2:
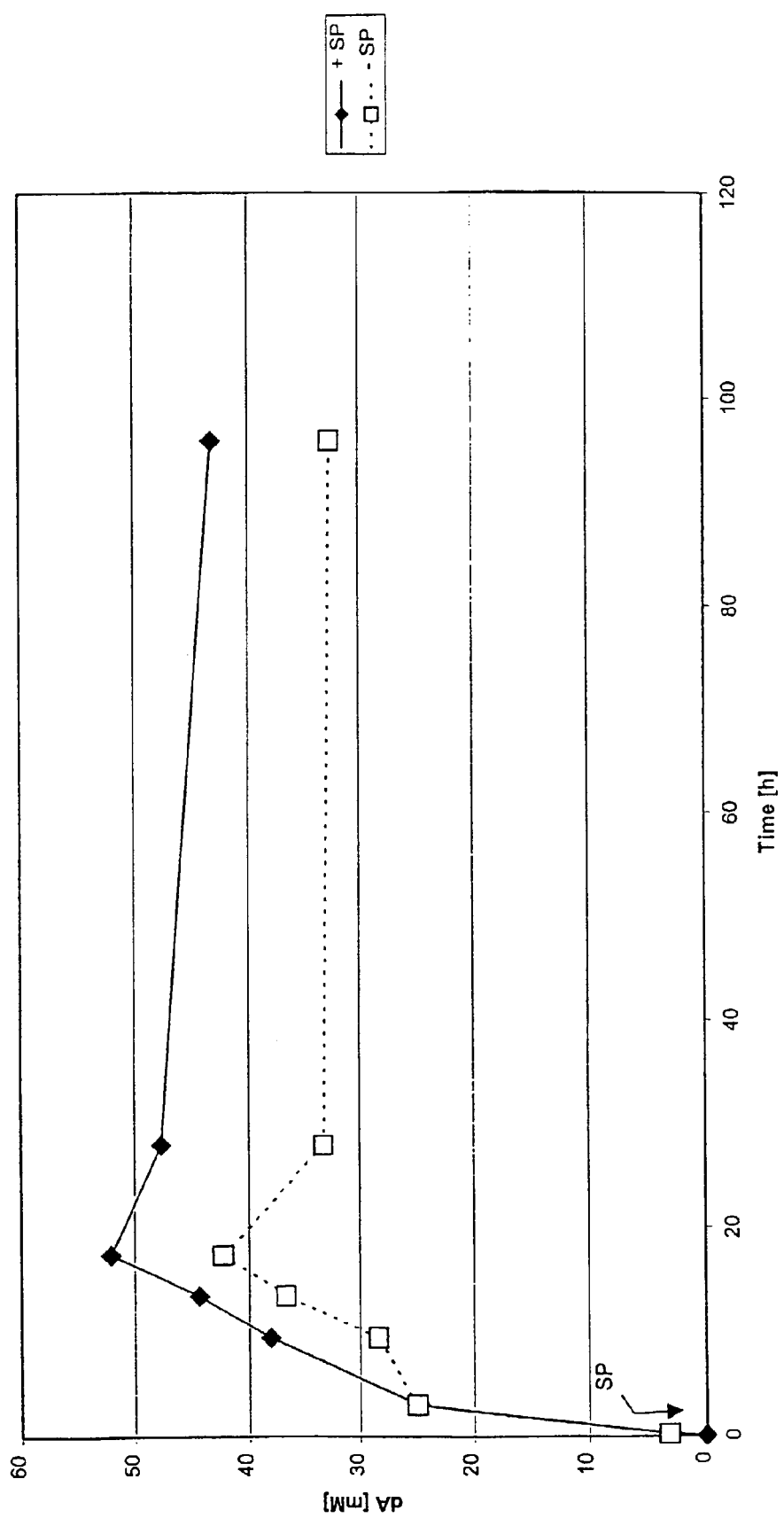
FIG. 2 shows the synthesis of deoxyadenosine according to Example 12.

After yielding approx. 95 mM dR5P the enzymes were deactivated by heating to 65° C. for 10 min. and excess of AcAld was removed by evaporation. In the second step dR5P in a final concentration of 64 mM was converted to deoxyadenosine (dA) by adding adenine (A, final concentration 58 mM) in the presence of 300 μM MnCl$_2$, 5 μM Glucose-1,6-bisphosphate, pentosephosphate mutase from *E. coli* (PPM, 2 kU/l), purine nucleoside phosphorylase from *E. coli* (PNP, 1 kU/l). The synthesis was run at 20° C., pH 7.4. In one experiment 200 mM sucrose and 0.6 kU/l sucrose phosphorylase (SP) from *Leuconostoc mes.* were added at t=2 h (see arrow in FIG. 2, rhombus, solid line), in a second experiment addition of SP was omitted (squares, dotted line). The conversion was monitored by RP-HPLC (column Hypersil ODS 5 μm, 250×4,6 mm; eluent: 30 mM potassium phosphate, 5 mM tetrabutyl ammoniumhydrogensulfate pH 6.0/1% acetonitrile, flow rate: 1 ml/min, column temp.: 35° C., det.: UV at 260 nm) and is shown in FIG. 2.

Figure 3:
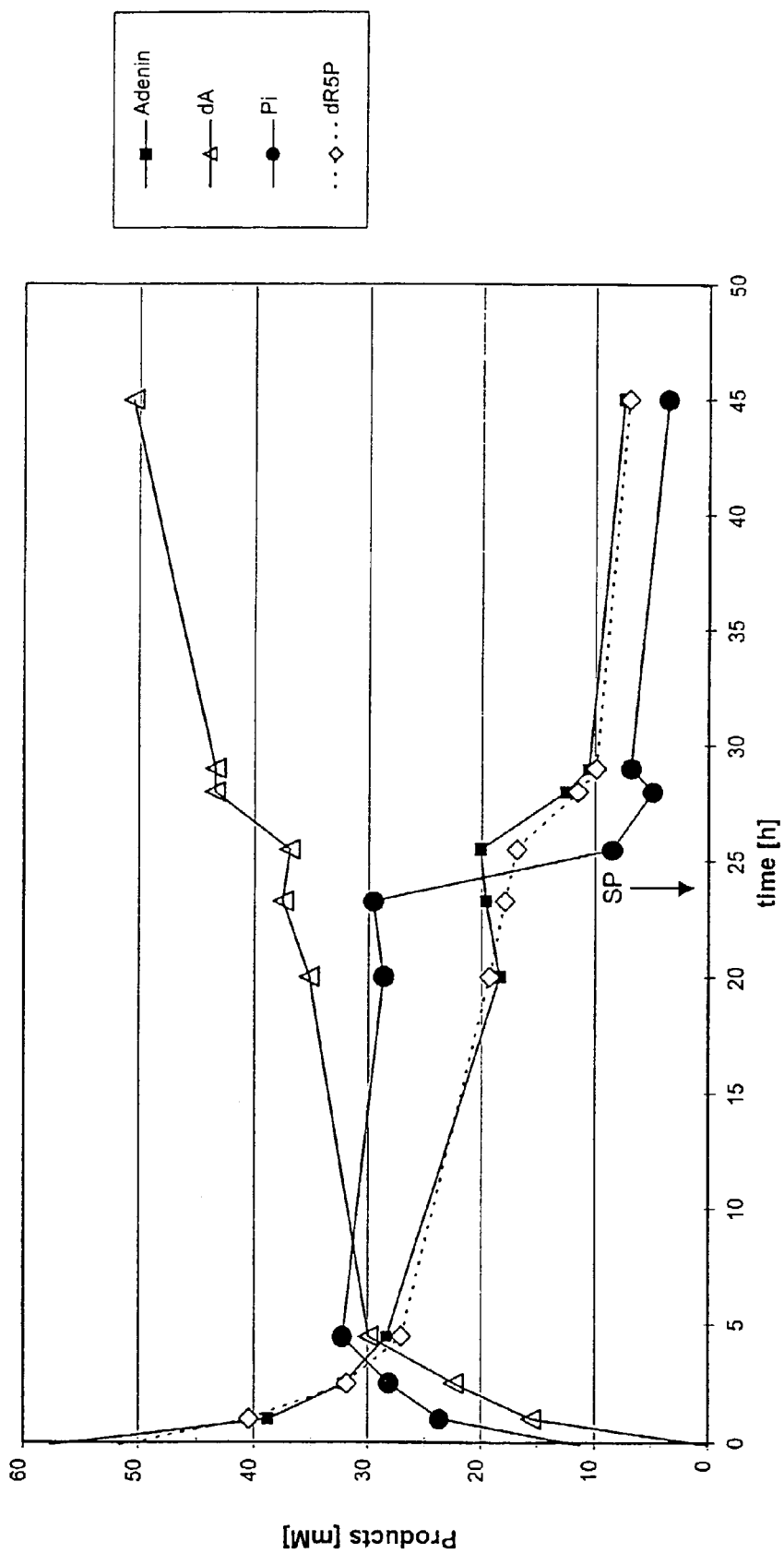
FIG. 3 shows the synthesis of deoxyadensine according to Example 13.

Example 13 dR5P was prepared by adding FDP-Aldolase II (AldII) from *E. coli*, pentosephosphate aldolase (PPA) from *E. coli* and triosephosphate isomerase (TIM) from *E. coli* to fructose-1,6-bisphosphate (FDP) and acetaldehyde (AcAld) essentially according to Ex. 6 Excess of AcAld was removed by evaporation. dR5P in a final concentration of 60 mM was converted to deoxyadenosine (dA) by adding adenine (A, final concentration 58 mM) in the presence of 300 μM MnCl$_2$, 5 μM Glucose-1,6-bisphosphate, pentosephosphate mutase from *E. coli* (PPM, 1,5 kU/l), purine nucleoside phosphorylase from *E. coli* (PNP, 1 kU/l). The synthesis was run at 20° C., pH 7.4. After 24 h sucrose in a final concentration of 200 mM and sucrose phosphorlyase from *Leuconsotoc mes.* (1 kU/l) were added. Conversion was monitored by RP-HPLC (dA, A, see ex. 12)) resp. enzymatical assay (dR5P, using step by step glycerol-3-phosphate dehydrogenase (GDH), rabbit muscle aldolase (RAMA), triosephosphate isomerase (TIM), pentosephosphate aldolase (PPA) in the presence of NADH (0,26 mM in 300 mM Triethanol amine buffer pH 7.6)) and phosphomolybdate complexing of inorg. phosphate (Sigma, Proc. No. 360-UV). This is shown in FIG. 3.

Figure 4:
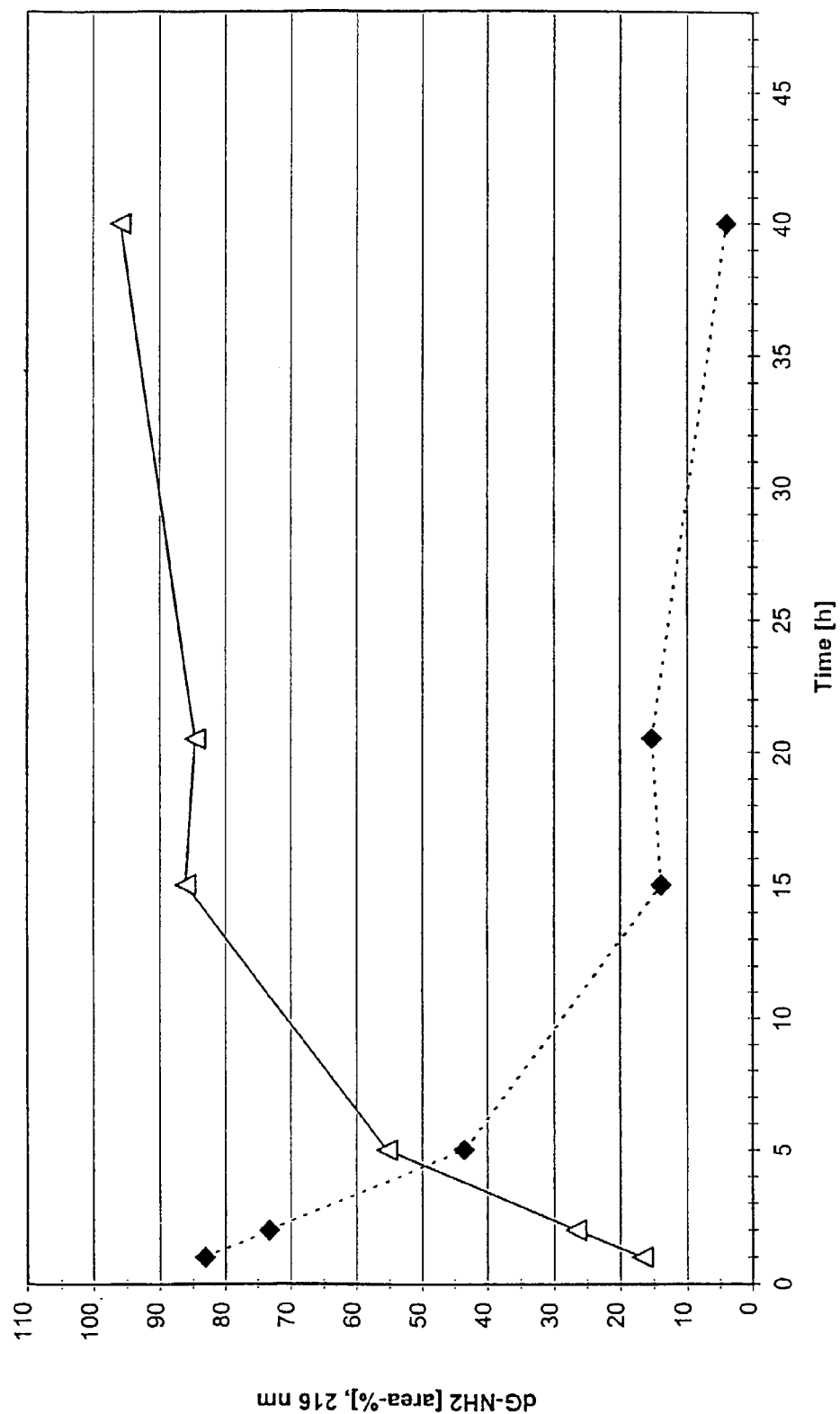
FIG. 4 shows the synthesis of dG-HN$_2$ according to Example 14.

Example 14 dR5P was essentially prepared according according to Ex. 6. dR5P in a final concentration of 80 mM was then converted to deoxy-6-aminoguanosine (dG-NH$_2$) by adding 2,6-Diaminopurine (DAP, final concentration 77 mM) in the presence of 200 mM sucrose, 300 μM MnCl$_2$, 5 μM Glucose-1,6-bisphosphate, pentosephosphate mutase from *E. coli* (PPM, 2,5 kU/l), purine nucleoside phosphorylase from *E. coli* (PNP, 1 kU/l), sucrose phosphorylase from *Leucoonostoc mes.* (SP, 1,5 kU/l). The synthesis was run at 20° C. pH 7.4. After 2,5 h, 5 h and 20,5 h additional amounts of enzymes were added: 2,5 h PPM (2,5 kU/l), PNP (1 kU/l, SP (1,5 kU/l), 5 h PPM (2,5 kU/l), SP (1,5 kU/l), 20,5 h: PPM (2,5 kU/l), SP (1,5 kU/l). The conversion was monitored by RP-HPLC (column Hypersil ODS 5 μm, 250×4,6 mm; eluent: 30 mM potassium phosphate, 5 mM tetrabutyl ammoniumhydrogensulfate pH 6.0/1% acetonitrile, flow rate: 1 ml/min, column temp.: 35° C., det.: UV at 216 nm) and is shown in FIG. 4.

What is claimed is:

1. A method for the in vitro enzymatic synthesis of a purine deoxyribonucleoside comprising reacting deoxyribose 1-phosphate (dR1P) and a nucleobase and catalyzing said enzymatic synthesis with a purine nucleoside phosphorylase (PNP, EC 2.4.2.1), wherein a deoxyribonucleoside and inorganic phosphate are formed and wherein the inorganic phosphate is removed by phosphorylation of a substrate with said inorganic phosphate.

2. The method of claim 1, wherein the nucleobase is selected from the group consisting of thymine, uracil, adenine, guanine, hypoxanthinine and analogs thereof.

3. The method of claim 2, wherein said analog is selected from the group consisting of: 2-thio-uracil, 6-aza-uracil, 5-carboxy-2-thio-uracil, 6-aza-thymine, 6-aza-2-thio-thymine and 2,6-diamino-purine.

4. The method of claim 1, comprising reacting said inorganic phosphate with fructose-diphosphate (FDP) to form pyrophosphate and fructose-6-phosphate (F6P).

5. The method of claim 4, wherein the reaction is catalyzed by a Ppi-dependent phosphofructokinase (PFK-Ppi, EC 2.7.1.90).

6. The method of claim 1, comprising reacting said inorganic phosphate with a polysaccharide to form a monosaccharide and a phosphorylated monosaccharide.

7. The method of claim 6, wherein the polysaccharide is a disaccharide.

8. The method of claim 7, wherein the disaccharide is sucrose or maltose.

9. The method of claim 8, wherein the substrate phosphorylation is catalyzed by a sucrose phosphorylase (EC 2.4.1.7) or a maltose phosphorylase (EC 2.4.1.8).

10. The method of claim 6, further comprising reacting the phosphorylated monosaccharide to form a galactoside.

11. The method of claim 1, further comprising generating deoxyribose-1-phosphate by isomerizing deoxyribose 5-phosphate (dR5P) prior to reacting said deoxyribose-1-phosphate with a nucleobase.

12. The method of claim 11, comprising isomerizing said deoxyribose 5-phosphate with phosphopentose mutase (PPM, EC 5.4.2.7).

13. The method of claim 11, further comprising forming the deoxyribose-5-phosphate by condensing glyceraldehyde 3-phosphate (GAP) with acetaldehyde prior to isomerization.

14. The method of claim 13, further comprising catalyzing said condensation with a phosphopentose aldolase (PPA, EC 4.1.2.4).

15. The method of claim 13, further comprising enzymatically generating said glyceraldehyde 3-phosphate (GAP) from fructose 1,6-diphosphate, dihydroxyacetone (DHA) or glycerolphosphate prior to condensation.

16. The method of claim 15, comprising generating the glyceraldehyde 3-phosphate from fructose 1,6-diphosphate in a reaction catalyzed by an FDP-aldolase I or an FDP-aldolase II.

17. The method of claim 1, further comprising reacting a deoxyribonucleoside containing a first nucleobase with a second nucleobase to form a deoxyribonucleoside containing the second nucleobase, wherein said reaction is catalyzed by a nucleoside 2-deoxyribosyl transferase (NdT, EC 2.4.2.6), and wherein said NdT is obtained from *Laetobacillus leichmannii* and is encoded by (a) a nucleic acid molecule consisting of the nucleotide sequence of SEQ ID NO: 13, (b) a nucleic acid molecule consisting of a nucleotide sequence encoding the protein encoded by SEQ ID NO: 13 or (c) a nucleic acid molecule hybridizing under stringent conditions to the nucleic acid molecule of (a) or (b), wherein the stringent conditions are 55° C., 1×SSC buffer and 0.1% SDS.

18. The method of claim 17, wherein said second nucleobase is selected from cytosine and cytosine analogs.

19. The method of claim 17, wherein said second nucleobase is selected from the group consisting of 5-aza-cytosine, 2,6-dichloro-purine, 6-aza-thymine and 5-fluoro-uracil.

20. A method for the in vitro enzymatic synthesis of purine deoxyribonucleosides comprising the steps of:
   (i) condensing glyceraldehyde 3-phosphate (GAP) with acetaldehyde to deoxyribose 5-phosphate (dR5P),
   (ii) isomerizing deoxyribose 5-phosphate to deoxyribose 1-phosphate (dR1P), and
   (iii) reacting deoxyribose 1-phosphate and nucleobase and catalyzing said reaction with a purine nucleoside phosphorylase (PNP, EC 2.4.2.1), wherein a deoxyribonucleoside and inorganic phosphate are formed, and wherein the inorganic phosphate is removed by phosphorylation of a substrate with said inorganic phosphate.

21. The method of claim 20, wherein the complete reaction of steps (i) to (iii) is carried out without isolating intermediate products.

22. The method of claim 20, wherein the glyceraldehyde 3-phosphate (GAP) is generated from fructose 1,6-diphosphate (FDP), dihydroxy-acetone (DHA) or glycerolphosphate (GP) prior to condensation.

23. The method of claim 20, further comprising removing excess acetaldehyde before step (ii).

24. The method of claim 22, further comprising removing excess starting materials or by-products of the generation of GAP before step (ii).

25. The method of claim 24, wherein said excess starting material is fructose 1,6-diphosphate and said excess by-product is deoxyxylulose 1-phosphate (dX1P).

26. The method of claim 22, wherein no starting materials or by-products of the generation of GAP are present before step (ii).

27. The method of claim 22, wherein GAP is generated from FDP, and DXP1 is generated as an excess by-product thereby.

* * * * *

SEQUENCE LISTING

```
<160> NUMBER OF SEQ ID NOS: 20

<210> SEQ ID NO 1
<211> LENGTH: 1323
<212> TYPE: DNA
<213> ORGANISM: Escherichia coli
<220> FEATURE:
<221> NAME/KEY: CDS
<222> LOCATION: (1)..(1320)

<400> SEQUENCE: 1 ttg ttt ctc gca caa gaa att att cgt aaa aaa cgt gat ggt cat gcg      48
Leu Phe Leu Ala Gln Glu Ile Ile Arg Lys Lys Arg Asp Gly His Ala
  1               5                  10                  15 ctg agc gat gaa gaa att cgt ttc ttt atc aac ggt att cgc gac aac      96
Leu Ser Asp Glu Glu Ile Arg Phe Phe Ile Asn Gly Ile Arg Asp Asn
             20                  25                  30 act atc tcc gaa ggg cag att gcc gcc ctc gcg atg acc att ttc ttc     144
Thr Ile Ser Glu Gly Gln Ile Ala Ala Leu Ala Met Thr Ile Phe Phe
         35                  40                  45 cac gat atg aca atg cct gag cgt gtc tcg ctg acc atg gcg atg cga     192
```

```
                His Asp Met Thr Met Pro Glu Arg Val Ser Leu Thr Met Ala Met Arg
                    50                  55                  60 gat tca gga acc gtt ctc gac tgg aaa agc ctg cat ctg aat ggc ccg        240
Asp Ser Gly Thr Val Leu Asp Trp Lys Ser Leu His Leu Asn Gly Pro
 65              70                  75                  80 att gtt gat aaa cac tcc acc ggt ggc gtc ggc gat gtg act tcg ctg        288
Ile Val Asp Lys His Ser Thr Gly Gly Val Gly Asp Val Thr Ser Leu
                 85                  90                  95 atg ttg ggg ccg atg gtc gca gcc tgc ggc ggc tat att ccg atg atc        336
Met Leu Gly Pro Met Val Ala Ala Cys Gly Gly Tyr Ile Pro Met Ile
            100                 105                 110 tct ggt cgc ggc ctc ggt cat act ggc ggt acg ctc gac aaa ctg gaa        384
Ser Gly Arg Gly Leu Gly His Thr Gly Gly Thr Leu Asp Lys Leu Glu
            115                 120                 125 tcc atc cct ggc ttc gac att ttc ccg gat gac aac cgt ttc cgc gaa        432
Ser Ile Pro Gly Phe Asp Ile Phe Pro Asp Asp Asn Arg Phe Arg Glu
        130                 135                 140 att att aaa gac gtc ggc gtg gcg att atc ggt cag acc agt tca ctg        480
Ile Ile Lys Asp Val Gly Val Ala Ile Ile Gly Gln Thr Ser Ser Leu
145                 150                 155                 160 gct ccg gct gat aaa cgt ttc tac gcg acc cgt gat att acc gca acc        528
Ala Pro Ala Asp Lys Arg Phe Tyr Ala Thr Arg Asp Ile Thr Ala Thr
                165                 170                 175 gtg gac tcc atc ccg ctg atc acc gcc tct att ctg gcg aag aaa ctt        576
Val Asp Ser Ile Pro Leu Ile Thr Ala Ser Ile Leu Ala Lys Lys Leu
            180                 185                 190 gcg gaa ggt ctg gac gcg ctg gtg atg gac gtg aaa gtg ggt agc ggc        624
Ala Glu Gly Leu Asp Ala Leu Val Met Asp Val Lys Val Gly Ser Gly
            195                 200                 205 gcg ttt atg ccg acc tac gaa ctc tct gaa gcc ctt gcc gaa gcg att        672
Ala Phe Met Pro Thr Tyr Glu Leu Ser Glu Ala Leu Ala Glu Ala Ile
        210                 215                 220 gtt ggc gtg gct aac ggc gct ggc gtg cgc acc acc gcg ctg ctc acc        720
Val Gly Val Ala Asn Gly Ala Gly Val Arg Thr Thr Ala Leu Leu Thr
225                 230                 235                 240 gac atg aat cag gta ctg gcc tcc agt gca ggt aac gcg gtt gaa gtt        768
Asp Met Asn Gln Val Leu Ala Ser Ser Ala Gly Asn Ala Val Glu Val
                245                 250                 255 cgt gaa gcg gtg cag ttc ctg acg ggt gaa tat cgt aac ccg cgt ctg        816
Arg Glu Ala Val Gln Phe Leu Thr Gly Glu Tyr Arg Asn Pro Arg Leu
            260                 265                 270 ttt gat gtc acg atg gcg ctg tgc gtg gag atg ctg atc tcc ggc aaa        864
Phe Asp Val Thr Met Ala Leu Cys Val Glu Met Leu Ile Ser Gly Lys
            275                 280                 285 ctg gcg aaa gat gac gcc gaa gcg cgc gcg aaa ttg cag gcg gtg ctg        912
Leu Ala Lys Asp Asp Ala Glu Ala Arg Ala Lys Leu Gln Ala Val Leu
        290                 295                 300 gac aac ggt aaa gcg gca gaa gtc ttt ggt cgt atg gta gcg gca caa        960
Asp Asn Gly Lys Ala Ala Glu Val Phe Gly Arg Met Val Ala Ala Gln
305                 310                 315                 320 aaa ggc ccg acc gac ttc gtt gag aac tac gcg aag tat ctg ccg aca       1008
Lys Gly Pro Thr Asp Phe Val Glu Asn Tyr Ala Lys Tyr Leu Pro Thr
                325                 330                 335 gcg atg ctg acg aaa gca gtc tat gct gat acc gaa ggt ttt gtc agt       1056
Ala Met Leu Thr Lys Ala Val Tyr Ala Asp Thr Glu Gly Phe Val Ser
            340                 345                 350 gaa atg gat acc cgc gcg ctg ggg atg gca gtg gtt gca atg ggc ggc       1104
Glu Met Asp Thr Arg Ala Leu Gly Met Ala Val Val Ala Met Gly Gly
            355                 360                 365
```

```
gga cgc cgt cag gca tct gac acc atc gat tac agc gtc ggc ttt act      1152
Gly Arg Arg Gln Ala Ser Asp Thr Ile Asp Tyr Ser Val Gly Phe Thr
370                 375                 380 gat atg gcg cgt ctg ggc gac cag gta gac ggt cag cgt ccg ctg gcg      1200
Asp Met Ala Arg Leu Gly Asp Gln Val Asp Gly Gln Arg Pro Leu Ala
385                 390                 395                 400 gtt atc cac gcg aaa gac gaa aac aac tgg cag gaa gcg gcg aaa gcg      1248
Val Ile His Ala Lys Asp Glu Asn Asn Trp Gln Glu Ala Ala Lys Ala
                405                 410                 415 gtg aaa gcg gca att aaa ctt gcc gat aaa gca ccg gaa agc aca cca      1296
Val Lys Ala Ala Ile Lys Leu Ala Asp Lys Ala Pro Glu Ser Thr Pro
        420                 425                 430 act gtc tat cgc cgt atc agc gaa taa                                  1323
Thr Val Tyr Arg Arg Ile Ser Glu
        435                 440

<210> SEQ ID NO 2
<211> LENGTH: 440
<212> TYPE: PRT
<213> ORGANISM: Escherichia coli

<400> SEQUENCE: 2

Leu Phe Leu Ala Gln Glu Ile Ile Arg Lys Lys Arg Asp Gly His Ala
1               5                   10                  15

Leu Ser Asp Glu Glu Ile Arg Phe Phe Ile Asn Gly Ile Arg Asp Asn
                20                  25                  30

Thr Ile Ser Glu Gly Gln Ile Ala Ala Leu Ala Met Thr Ile Phe Phe
            35                  40                  45

His Asp Met Thr Met Pro Glu Arg Val Ser Leu Thr Met Ala Met Arg
        50                  55                  60

Asp Ser Gly Thr Val Leu Asp Trp Lys Ser Leu His Leu Asn Gly Pro
65                  70                  75                  80

Ile Val Asp Lys His Ser Thr Gly Gly Val Gly Asp Val Thr Ser Leu
                85                  90                  95

Met Leu Gly Pro Met Val Ala Cys Gly Gly Tyr Ile Pro Met Ile
            100                 105                 110

Ser Gly Arg Gly Leu Gly His Thr Gly Gly Thr Leu Asp Lys Leu Glu
        115                 120                 125

Ser Ile Pro Gly Phe Asp Ile Phe Pro Asp Asp Asn Arg Phe Arg Glu
130                 135                 140

Ile Ile Lys Asp Val Gly Val Ala Ile Ile Gly Gln Thr Ser Ser Leu
145                 150                 155                 160

Ala Pro Ala Asp Lys Arg Phe Tyr Ala Thr Arg Asp Ile Thr Ala Thr
                165                 170                 175

Val Asp Ser Ile Pro Leu Ile Thr Ala Ser Ile Leu Ala Lys Lys Leu
            180                 185                 190

Ala Glu Gly Leu Asp Ala Leu Val Met Asp Val Lys Val Gly Ser Gly
        195                 200                 205

Ala Phe Met Pro Thr Tyr Glu Leu Ser Glu Ala Leu Ala Glu Ala Ile
210                 215                 220

Val Gly Val Ala Asn Gly Ala Gly Val Arg Thr Thr Ala Leu Leu Thr
225                 230                 235                 240

Asp Met Asn Gln Val Leu Ala Ser Ser Ala Gly Asn Ala Val Glu Val
                245                 250                 255

Arg Glu Ala Val Gln Phe Leu Thr Gly Glu Tyr Arg Asn Pro Arg Leu
            260                 265                 270
```

```
            Phe Asp Val Thr Met Ala Leu Cys Val Glu Met Leu Ile Ser Gly Lys
                275                 280                 285

Leu Ala Lys Asp Asp Ala Glu Ala Arg Ala Lys Leu Gln Ala Val Leu
                290                 295                 300

Asp Asn Gly Lys Ala Ala Glu Val Phe Gly Arg Met Val Ala Ala Gln
            305                 310                 315                 320

Lys Gly Pro Thr Asp Phe Val Glu Asn Tyr Ala Lys Tyr Leu Pro Thr
                            325                 330                 335

Ala Met Leu Thr Lys Ala Val Tyr Ala Asp Thr Gly Phe Val Ser
                        340                 345                 350

Glu Met Asp Thr Arg Ala Leu Gly Met Ala Val Val Ala Met Gly Gly
                        355                 360                 365

Gly Arg Arg Gln Ala Ser Asp Thr Ile Asp Tyr Ser Val Gly Phe Thr
                370                 375                 380

Asp Met Ala Arg Leu Gly Asp Gln Val Asp Gly Gln Arg Pro Leu Ala
            385                 390                 395                 400

Val Ile His Ala Lys Asp Glu Asn Asn Trp Gln Glu Ala Ala Lys Ala
                            405                 410                 415

Val Lys Ala Ala Ile Lys Leu Ala Asp Lys Ala Pro Glu Ser Thr Pro
                        420                 425                 430

Thr Val Tyr Arg Arg Ile Ser Glu
                        435                 440

<210> SEQ ID NO 3
<211> LENGTH: 720
<212> TYPE: DNA
<213> ORGANISM: Escherichia coli
<220> FEATURE:
<221> NAME/KEY: CDS
<222> LOCATION: (1)..(717)

<400> SEQUENCE: 3 atg gct acc cca cac att aat gca gaa atg ggc gat ttc gct gac gta        48
Met Ala Thr Pro His Ile Asn Ala Glu Met Gly Asp Phe Ala Asp Val
  1               5                  10                  15 gtt ttg atg cca ggc gac ccg ctg cgt gcg aag tat att gct gaa act        96
Val Leu Met Pro Gly Asp Pro Leu Arg Ala Lys Tyr Ile Ala Glu Thr
             20                  25                  30 ttc ctt gaa gat gcc cgt gaa gtg aac aac gtt cgc ggt atg ctg ggc       144
Phe Leu Glu Asp Ala Arg Glu Val Asn Asn Val Arg Gly Met Leu Gly
         35                  40                  45 ttc acc ggt act tac aaa ggc cgc aaa att tcc gta atg ggt cac ggt       192
Phe Thr Gly Thr Tyr Lys Gly Arg Lys Ile Ser Val Met Gly His Gly
     50                  55                  60 atg ggt atc ccg tcc tgc tcc atc tac acc aaa gaa ctg atc acc gat       240
Met Gly Ile Pro Ser Cys Ser Ile Tyr Thr Lys Glu Leu Ile Thr Asp
 65                  70                  75                  80 ttc ggc gtg aag aaa att atc cgc gtg ggt tcc tgt ggc gca gtt ctg       288
Phe Gly Val Lys Lys Ile Ile Arg Val Gly Ser Cys Gly Ala Val Leu
                 85                  90                  95 ccg cac gta aaa ctg cgc gac gtc gtt atc ggt atg ggt gcc tgc acc       336
Pro His Val Lys Leu Arg Asp Val Val Ile Gly Met Gly Ala Cys Thr
            100                 105                 110 gat tcc aaa gtt aac cgc atc cgt ttt aaa gac cat gac ttt gcc gct       384
Asp Ser Lys Val Asn Arg Ile Arg Phe Lys Asp His Asp Phe Ala Ala
        115                 120                 125 atc gct gac ttc gac atg gtg cgt aac gca gta gat gca gct aaa gca       432
Ile Ala Asp Phe Asp Met Val Arg Asn Ala Val Asp Ala Ala Lys Ala
    130                 135                 140
```

```
ctg ggt att gat gct cgc gtg ggt aac ctg ttc tcc gct gac ctg ttc      480
Leu Gly Ile Asp Ala Arg Val Gly Asn Leu Phe Ser Ala Asp Leu Phe
145                 150                 155                 160 tac tct ccg gac ggc gaa atg ttc gac gtg atg gaa aaa tac ggc att      528
Tyr Ser Pro Asp Gly Glu Met Phe Asp Val Met Glu Lys Tyr Gly Ile
                165                 170                 175 ctc ggc gtg gaa atg gaa gcg gct ggt atc tac ggc gtc gct gca gaa      576
Leu Gly Val Glu Met Glu Ala Ala Gly Ile Tyr Gly Val Ala Ala Glu
            180                 185                 190 ttt ggc gcg aaa gcc ctg acc atc tgc acc gta tct gac cac atc cgc      624
Phe Gly Ala Lys Ala Leu Thr Ile Cys Thr Val Ser Asp His Ile Arg
        195                 200                 205 act cac gag cag acc act gcc gct gag cgt cag act acc ttc aac gac      672
Thr His Glu Gln Thr Thr Ala Ala Glu Arg Gln Thr Thr Phe Asn Asp
    210                 215                 220 atg atc aaa atc gca ctg gaa tcc gtt ctg ctg ggc gat aaa gag taa      720
Met Ile Lys Ile Ala Leu Glu Ser Val Leu Leu Gly Asp Lys Glu
225                 230                 235
```

<210> SEQ ID NO 4
<211> LENGTH: 239
<212> TYPE: PRT
<213> ORGANISM: Escherichia coli

<400> SEQUENCE: 4

```
Met Ala Thr Pro His Ile Asn Ala Glu Met Gly Asp Phe Ala Asp Val
1               5                   10                  15

Val Leu Met Pro Gly Asp Pro Leu Arg Ala Lys Tyr Ile Ala Glu Thr
            20                  25                  30

Phe Leu Glu Asp Ala Arg Glu Val Asn Asn Val Arg Gly Met Leu Gly
        35                  40                  45

Phe Thr Gly Thr Tyr Lys Gly Arg Lys Ile Ser Val Met Gly His Gly
    50                  55                  60

Met Gly Ile Pro Ser Cys Ser Ile Tyr Thr Lys Glu Leu Ile Thr Asp
65                  70                  75                  80

Phe Gly Val Lys Lys Ile Ile Arg Val Gly Ser Cys Gly Ala Val Leu
                85                  90                  95

Pro His Val Lys Leu Arg Asp Val Val Ile Gly Met Gly Ala Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140

Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
                165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
        195                 200                 205

Thr His Glu Gln Thr Thr Ala Ala Glu Arg Gln Thr Thr Phe Asn Asp
    210                 215                 220

Met Ile Lys Ile Ala Leu Glu Ser Val Leu Leu Gly Asp Lys Glu
225                 230                 235
```

```
<210> SEQ ID NO 5
<211> LENGTH: 1224
<212> TYPE: DNA
<213> ORGANISM: Escherichia coli
<220> FEATURE:
<221> NAME/KEY: CDS
<222> LOCATION: (1)..(1221)

<400> SEQUENCE: 5 atg aaa cgt gca ttt att atg gtg ctg gac tca ttc ggc atc ggc gct      48
Met Lys Arg Ala Phe Ile Met Val Leu Asp Ser Phe Gly Ile Gly Ala
 1               5                  10                  15 aca gaa gat gca gaa cgc ttt ggt gac gtc ggg gct gac acc ctg ggt      96
Thr Glu Asp Ala Glu Arg Phe Gly Asp Val Gly Ala Asp Thr Leu Gly
                 20                  25                  30 cat atc gca gaa gct tgt gcc aaa ggc gaa gct gat aac ggt cgt aaa     144
His Ile Ala Glu Ala Cys Ala Lys Gly Glu Ala Asp Asn Gly Arg Lys
             35                  40                  45 ggc ccg ctc aat ctg cca aat ctg acc cgt ctg ggg ctg gcg aaa gca     192
Gly Pro Leu Asn Leu Pro Asn Leu Thr Arg Leu Gly Leu Ala Lys Ala
 50                  55                  60 cac gaa ggt tct acc ggt ttc att ccg gcg gga atg gac ggc aac gct     240
His Glu Gly Ser Thr Gly Phe Ile Pro Ala Gly Met Asp Gly Asn Ala
 65                  70                  75                  80 gaa gtt atc ggc gcg tac gca tgg gcg cac gaa atg tca tcc ggt aaa     288
Glu Val Ile Gly Ala Tyr Ala Trp Ala His Glu Met Ser Ser Gly Lys
                 85                  90                  95 gat acc ccg tct ggt cac tgg gaa att gcc ggt gtc ccg gtt ctg ttt     336
Asp Thr Pro Ser Gly His Trp Glu Ile Ala Gly Val Pro Val Leu Phe
            100                 105                 110 gag tgg gga tat ttc tcc gat cac gaa aac agc ttc ccg caa gag ctg     384
Glu Trp Gly Tyr Phe Ser Asp His Glu Asn Ser Phe Pro Gln Glu Leu
        115                 120                 125 ctg gat aaa ctg gtc gaa cgc gct aat ctg ccg ggt tac ctc ggt aac     432
Leu Asp Lys Leu Val Glu Arg Ala Asn Leu Pro Gly Tyr Leu Gly Asn
    130                 135                 140 tgc cac tct tcc ggt acg gtc att ctg gat caa ctg ggc gaa gag cac     480
Cys His Ser Ser Gly Thr Val Ile Leu Asp Gln Leu Gly Glu Glu His
145                 150                 155                 160 atg aaa acc ggc aag ccg att ttc tat acc tcc gct gac tcc gtg ttc     528
Met Lys Thr Gly Lys Pro Ile Phe Tyr Thr Ser Ala Asp Ser Val Phe
                165                 170                 175 cag att gcc tgc cat gaa gaa act ttc ggt ctg gat aaa ctc tac gaa     576
Gln Ile Ala Cys His Glu Glu Thr Phe Gly Leu Asp Lys Leu Tyr Glu
            180                 185                 190 ctg tgc gaa atc gcc cgt gaa gag ctg acc aac ggc ggc tac aat atc     624
Leu Cys Glu Ile Ala Arg Glu Glu Leu Thr Asn Gly Gly Tyr Asn Ile
        195                 200                 205 ggt cgt gtt atc gct cgt ccg ttt atc ggc gac aaa gcc ggt aac ttc     672
Gly Arg Val Ile Ala Arg Pro Phe Ile Gly Asp Lys Ala Gly Asn Phe
    210                 215                 220 cag cgt acc ggt aac cgt cac gac ctg gct gtt gag ccg cca gca ccg     720
Gln Arg Thr Gly Asn Arg His Asp Leu Ala Val Glu Pro Pro Ala Pro
225                 230                 235                 240 acc gtg ctg cag aaa ctg gtt gat gaa aaa cac ggc cag gtg gtt tct     768
Thr Val Leu Gln Lys Leu Val Asp Glu Lys His Gly Gln Val Val Ser
                245                 250                 255 gtc ggt aaa att gcg gac atc tac gcc aac tgc ggt atc acc aaa aaa     816
Val Gly Lys Ile Ala Asp Ile Tyr Ala Asn Cys Gly Ile Thr Lys Lys
            260                 265                 270 gtg aaa gcg act ggc ctg gac gcg ctg ttt gac gcc acc atc aaa gag     864
```

```
Val Lys Ala Thr Gly Leu Asp Ala Leu Phe Asp Ala Thr Ile Lys Glu
            275                 280                 285 atg aaa gaa gcg ggt gat aac acc atc gtc ttc acc aac ttc gtt gac    912
Met Lys Glu Ala Gly Asp Asn Thr Ile Val Phe Thr Asn Phe Val Asp
        290                 295                 300 ttc gac tct tcc tgg ggc cac cgt cgc gac gtc gcc ggt tat gcc gcg    960
Phe Asp Ser Ser Trp Gly His Arg Arg Asp Val Ala Gly Tyr Ala Ala
305                 310                 315                 320 ggt ctg gaa ctg ttc gac cgc cgt ctg ccg gag ctg atg tct ctg ctg   1008
Gly Leu Glu Leu Phe Asp Arg Arg Leu Pro Glu Leu Met Ser Leu Leu
                325                 330                 335 cgc gat gac gac atc ctg atc ctc acc gct gac cac ggt tgc gat ccg   1056
Arg Asp Asp Asp Ile Leu Ile Leu Thr Ala Asp His Gly Cys Asp Pro
            340                 345                 350 acc tgg acc ggt act gac cac acg cgt gaa cac att ccg gta ctg gta   1104
Thr Trp Thr Gly Thr Asp His Thr Arg Glu His Ile Pro Val Leu Val
        355                 360                 365 tat ggc ccg aaa gta aaa ccg ggc tca ctg ggt cat cgt gaa acc ttc   1152
Tyr Gly Pro Lys Val Lys Pro Gly Ser Leu Gly His Arg Glu Thr Phe
370                 375                 380 gcg gat atc ggc cag act ctg gca aaa tat ttt ggt act tct gat atg   1200
Ala Asp Ile Gly Gln Thr Leu Ala Lys Tyr Phe Gly Thr Ser Asp Met
385                 390                 395                 400 gaa tat ggc aaa gcc atg ttc tga                                    1224
Glu Tyr Gly Lys Ala Met Phe
                405
```

<210> SEQ ID NO 6
<211> LENGTH: 407
<212> TYPE: PRT
<213> ORGANISM: Escherichia coli

<400> SEQUENCE: 6

```
Met Lys Arg Ala Phe Ile Met Val Leu Asp Ser Phe Gly Ile Gly Ala
  1               5                  10                  15

Thr Glu Asp Ala Glu Arg Phe Gly Asp Val Gly Ala Asp Thr Leu Gly
                 20                  25                  30

His Ile Ala Glu Ala Cys Ala Lys Gly Glu Ala Asp Asn Gly Arg Lys
             35                  40                  45

Gly Pro Leu Asn Leu Pro Asn Leu Thr Arg Leu Gly Leu Ala Lys Ala
         50                  55                  60

His Glu Gly Ser Thr Gly Phe Ile Pro Ala Gly Met Asp Gly Asn Ala
 65                  70                  75                  80

Glu Val Ile Gly Ala Tyr Ala Trp Ala His Glu Met Ser Ser Gly Lys
                 85                  90                  95

Asp Thr Pro Ser Gly His Trp Glu Ile Ala Gly Val Pro Val Leu Phe
            100                 105                 110

Glu Trp Gly Tyr Phe Ser Asp His Glu Asn Ser Phe Pro Gln Glu Leu
        115                 120                 125

Leu Asp Lys Leu Val Glu Arg Ala Asn Leu Pro Gly Tyr Leu Gly Asn
    130                 135                 140

Cys His Ser Ser Gly Thr Val Ile Leu Asp Gln Leu Gly Glu Glu His
145                 150                 155                 160

Met Lys Thr Gly Lys Pro Ile Phe Tyr Thr Ser Ala Asp Ser Val Phe
                165                 170                 175

Gln Ile Ala Cys His Glu Glu Thr Phe Gly Leu Asp Lys Leu Tyr Glu
            180                 185                 190
```

```
Leu Cys Glu Ile Ala Arg Glu Leu Thr Asn Gly Gly Tyr Asn Ile
        195                 200                 205
Gly Arg Val Ile Ala Arg Pro Phe Ile Gly Asp Lys Ala Gly Asn Phe
    210                 215                 220
Gln Arg Thr Gly Asn Arg His Asp Leu Ala Val Glu Pro Pro Ala Pro
225                 230                 235                 240
Thr Val Leu Gln Lys Leu Val Asp Glu Lys His Gly Gln Val Val Ser
            245                 250                 255
Val Gly Lys Ile Ala Asp Ile Tyr Ala Asn Cys Gly Ile Thr Lys Lys
        260                 265                 270
Val Lys Ala Thr Gly Leu Asp Ala Leu Phe Asp Ala Thr Ile Lys Glu
    275                 280                 285
Met Lys Glu Ala Gly Asp Asn Thr Ile Val Phe Thr Asn Phe Val Asp
290                 295                 300
Phe Asp Ser Ser Trp Gly His Arg Arg Asp Val Ala Gly Tyr Ala Ala
305                 310                 315                 320
Gly Leu Glu Leu Phe Asp Arg Arg Leu Pro Glu Leu Met Ser Leu Leu
            325                 330                 335
Arg Asp Asp Asp Ile Leu Ile Leu Thr Ala Asp His Gly Cys Asp Pro
        340                 345                 350
Thr Trp Thr Gly Thr Asp His Thr Arg Glu His Ile Pro Val Leu Val
    355                 360                 365
Tyr Gly Pro Lys Val Lys Pro Gly Ser Leu Gly His Arg Glu Thr Phe
370                 375                 380
Ala Asp Ile Gly Gln Thr Leu Ala Lys Tyr Phe Gly Thr Ser Asp Met
385                 390                 395                 400
Glu Tyr Gly Lys Ala Met Phe
            405

<210> SEQ ID NO 7
<211> LENGTH: 780
<212> TYPE: DNA
<213> ORGANISM: Escherichia coli
<220> FEATURE:
<221> NAME/KEY: CDS
<222> LOCATION: (1)..(777)

<400> SEQUENCE: 7 atg act gat ctg aaa gca agc agc ctg cgt gca ctg aaa ttg atg gac    48
Met Thr Asp Leu Lys Ala Ser Ser Leu Arg Ala Leu Lys Leu Met Asp
  1               5                  10                  15 ctg aac acc ctg aat gac gac gac acc gac gag aaa gtg atc gcc ctg    96
Leu Asn Thr Leu Asn Asp Asp Asp Thr Asp Glu Lys Val Ile Ala Leu
                 20                  25                  30 tgt cat cag gcc aaa act ccg gtc ggc aat acc gcc gct atc tgt atc   144
Cys His Gln Ala Lys Thr Pro Val Gly Asn Thr Ala Ala Ile Cys Ile
             35                  40                  45 tat cct cgc ttt atc ccg att gct cgc aaa act ctg aaa gag cag ggc   192
Tyr Pro Arg Phe Ile Pro Ile Ala Arg Lys Thr Leu Lys Glu Gln Gly
         50                  55                  60 acc ccg gaa atc cgt atc gct acg gta acc aac ttc cca cac ggt aac   240
Thr Pro Glu Ile Arg Ile Ala Thr Val Thr Asn Phe Pro His Gly Asn
 65                  70                  75                  80 gac gac atc gac atc gcg ctg gca gaa acc cgt gcg gca atc gcc tac   288
Asp Asp Ile Asp Ile Ala Leu Ala Glu Thr Arg Ala Ala Ile Ala Tyr
                 85                  90                  95 ggt gct gat gaa gtt gac gtt gtg ttc ccg tac cgc gcg ctg atg gcg   336
Gly Ala Asp Glu Val Asp Val Val Phe Pro Tyr Arg Ala Leu Met Ala
```

```
                100                 105                 110
ggt aac gag cag gtt ggt ttt gac ctg gtg aaa gcc tgt aaa gag gct    384
Gly Asn Glu Gln Val Gly Phe Asp Leu Val Lys Ala Cys Lys Glu Ala
        115                 120                 125 tgc gcg gca gcg aat gta ctg ctg aaa gtg atc atc gaa acc ggc gaa    432
Cys Ala Ala Ala Asn Val Leu Leu Lys Val Ile Ile Glu Thr Gly Glu
130                 135                 140 ctg aaa gac gaa gcg ctg atc cgt aaa gcg tct gaa atc tcc atc aaa    480
Leu Lys Asp Glu Ala Leu Ile Arg Lys Ala Ser Glu Ile Ser Ile Lys
145                 150                 155                 160 gcg ggt gcg gac ttc atc aaa acc tct acc ggt aaa gtg gct gtg aac    528
Ala Gly Ala Asp Phe Ile Lys Thr Ser Thr Gly Lys Val Ala Val Asn
                165                 170                 175 gcg acg ccg gaa agc gcg cgc atc atg atg gaa gtg atc cgt gat atg    576
Ala Thr Pro Glu Ser Ala Arg Ile Met Met Glu Val Ile Arg Asp Met
            180                 185                 190 ggc gta gaa aaa acc gtt ggt ttc aaa ccg gcg ggc ggc gtg cgt act    624
Gly Val Glu Lys Thr Val Gly Phe Lys Pro Ala Gly Gly Val Arg Thr
        195                 200                 205 gcg gaa gat gcg cag aaa tat ctc gcc att gca gat gaa ctg ttc ggt    672
Ala Glu Asp Ala Gln Lys Tyr Leu Ala Ile Ala Asp Glu Leu Phe Gly
210                 215                 220 gct gac tgg gca gat gcg cgt cac tac cgc ttt ggc gct tcc agc ctg    720
Ala Asp Trp Ala Asp Ala Arg His Tyr Arg Phe Gly Ala Ser Ser Leu
225                 230                 235                 240 ctg gca agc ctg ctg aaa gcg ctg ggt cac ggc gac ggt aag agc gcc    768
Leu Ala Ser Leu Leu Lys Ala Leu Gly His Gly Asp Gly Lys Ser Ala
                245                 250                 255 agc agc tac taa                                                    780
Ser Ser Tyr <210> SEQ ID NO 8
<211> LENGTH: 259
<212> TYPE: PRT
<213> ORGANISM: Escherichia coli

<400> SEQUENCE: 8

Met Thr Asp Leu Lys Ala Ser Ser Leu Arg Ala Leu Lys Leu Met Asp
 1               5                  10                  15

Leu Asn Thr Leu Asn Asp Asp Thr Asp Glu Lys Val Ile Ala Leu
            20                  25                  30

Cys His Gln Ala Lys Thr Pro Val Gly Asn Thr Ala Ala Ile Cys Ile
        35                  40                  45

Tyr Pro Arg Phe Ile Pro Ile Ala Arg Lys Thr Leu Lys Glu Gln Gly
    50                  55                  60

Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
            100                 105                 110

Gly Asn Glu Gln Val Gly Phe Asp Leu Val Lys Ala Cys Lys Glu Ala
        115                 120                 125

Cys Ala Ala Ala Asn Val Leu Leu Lys Val Ile Ile Glu Thr Gly Glu
130                 135                 140

Leu Lys Asp Glu Ala Leu Ile Arg Lys Ala Ser Glu Ile Ser Ile Lys
145                 150                 155                 160
```

```
                Ala Gly Ala Asp Phe Ile Lys Thr Ser Thr Gly Lys Val Ala Val Asn
                                165                 170                 175

Ala Thr Pro Glu Ser Ala Arg Ile Met Met Glu Val Ile Arg Asp Met
                            180                 185                 190

Gly Val Glu Lys Thr Val Gly Phe Lys Pro Ala Gly Val Arg Thr
                        195                 200                 205

Ala Glu Asp Ala Gln Lys Tyr Leu Ala Ile Ala Asp Glu Leu Phe Gly
                    210                 215                 220

Ala Asp Trp Ala Asp Ala Arg His Tyr Arg Phe Gly Ala Ser Ser Leu
                225                 230                 235                 240

Leu Ala Ser Leu Leu Lys Ala Leu Gly His Gly Asp Gly Lys Ser Ala
                                245                 250                 255

Ser Ser Tyr

<210> SEQ ID NO 9
<211> LENGTH: 1080
<212> TYPE: DNA
<213> ORGANISM: Escherichia coli
<220> FEATURE:
<221> NAME/KEY: CDS
<222> LOCATION: (1)..(1077)

<400> SEQUENCE: 9 atg tct aag att ttt gat ttc gta aaa cct ggc gta atc act ggt gat      48
Met Ser Lys Ile Phe Asp Phe Val Lys Pro Gly Val Ile Thr Gly Asp
 1               5                  10                  15 gac gta cag aaa gtt ttc cag gta gca aaa gaa aac aac ttc gca ctg      96
Asp Val Gln Lys Val Phe Gln Val Ala Lys Glu Asn Asn Phe Ala Leu
                20                  25                  30 cca gca gta aac tgc gtc ggt act gac tcc atc aac gcc gta ctg gaa    144
Pro Ala Val Asn Cys Val Gly Thr Asp Ser Ile Asn Ala Val Leu Glu
             35                  40                  45 acc gct gct aaa gtt aaa gcg ccg gtt atc gtt cag ttc tcc aac ggt    192
Thr Ala Ala Lys Val Lys Ala Pro Val Ile Val Gln Phe Ser Asn Gly
         50                  55                  60 ggt gct tcc ttt atc gct ggt aaa ggc gtg aaa tct gac gtt ccg cag    240
Gly Ala Ser Phe Ile Ala Gly Lys Gly Val Lys Ser Asp Val Pro Gln
 65                  70                  75                  80 ggt gct gct atc ctg ggc gcg atc tct ggt gcg cat cac gtt cac cag    288
Gly Ala Ala Ile Leu Gly Ala Ile Ser Gly Ala His His Val His Gln
                 85                  90                  95 atg gct gaa cat tat ggt gtt ccg gtt atc ctg cac act gac cac tgc    336
Met Ala Glu His Tyr Gly Val Pro Val Ile Leu His Thr Asp His Cys
            100                 105                 110 gcg aag aaa ctg ctg ccg tgg atc gac ggt ctg ttg gac gcg ggt gaa    384
Ala Lys Lys Leu Leu Pro Trp Ile Asp Gly Leu Leu Asp Ala Gly Glu
        115                 120                 125 aaa cac ttc gca gct acc ggt aag ccg ctg ttc tct tct cac atg atc    432
Lys His Phe Ala Ala Thr Gly Lys Pro Leu Phe Ser Ser His Met Ile
    130                 135                 140 gac ctg tct gaa gaa tct ctg caa gag aac atc gaa atc tgc tct aaa    480
Asp Leu Ser Glu Glu Ser Leu Gln Glu Asn Ile Glu Ile Cys Ser Lys
145                 150                 155                 160 tac ctg gag cgc atg tcc aaa atc ggc atg act ctg gaa atc gaa ctg    528
Tyr Leu Glu Arg Met Ser Lys Ile Gly Met Thr Leu Glu Ile Glu Leu
                165                 170                 175 ggt tgc acc ggt ggt gaa gaa gac ggc gtg gac aac agc cac atg gac    576
Gly Cys Thr Gly Gly Glu Glu Asp Gly Val Asp Asn Ser His Met Asp
            180                 185                 190
```

-continued

```
gct tct gca ctg tac acc cag ccg gaa gac gtt gat tac gca tac acc      624
Ala Ser Ala Leu Tyr Thr Gln Pro Glu Asp Val Asp Tyr Ala Tyr Thr
        195                 200                 205 gaa ctg agc aaa atc agc ccg cgt ttc acc atc gca gcg tcc ttc ggt      672
Glu Leu Ser Lys Ile Ser Pro Arg Phe Thr Ile Ala Ala Ser Phe Gly
    210                 215                 220 aac gta cac ggt gtt tac aag ccg ggt aac gtg gtt ctg act ccg acc      720
Asn Val His Gly Val Tyr Lys Pro Gly Asn Val Val Leu Thr Pro Thr
225                 230                 235                 240 atc ctg cgt gat tct cag gaa tat gtt tcc aag aaa cac aac ctg ccg      768
Ile Leu Arg Asp Ser Gln Glu Tyr Val Ser Lys Lys His Asn Leu Pro
                245                 250                 255 cac aac agc ctg aac ttc gta ttc cac ggt ggt tcc ggt tct act gct      816
His Asn Ser Leu Asn Phe Val Phe His Gly Gly Ser Gly Ser Thr Ala
            260                 265                 270 cag gaa atc aaa gac tcc gta agc tac ggc gta gta aaa atg aac atc      864
Gln Glu Ile Lys Asp Ser Val Ser Tyr Gly Val Val Lys Met Asn Ile
        275                 280                 285 gat acc gat acc caa tgg gca acc tgg gaa ggc gtt ctg aac tac tac      912
Asp Thr Asp Thr Gln Trp Ala Thr Trp Glu Gly Val Leu Asn Tyr Tyr
    290                 295                 300 aaa gcg aac gaa gct tat ctg cag ggt cag ctg ggt aac ccg aaa ggc      960
Lys Ala Asn Glu Ala Tyr Leu Gln Gly Gln Leu Gly Asn Pro Lys Gly
305                 310                 315                 320 gaa gat cag ccg aac aag aaa tac tac gat ccg cgc gta tgg ctg cgt     1008
Glu Asp Gln Pro Asn Lys Lys Tyr Tyr Asp Pro Arg Val Trp Leu Arg
                325                 330                 335 gcc ggt cag act tcg atg atc gct cgt ctg gag aaa gca ttc cag gaa     1056
Ala Gly Gln Thr Ser Met Ile Ala Arg Leu Glu Lys Ala Phe Gln Glu
            340                 345                 350 ctg aac gcg atc gac gtt ctg taa                                     1080
Leu Asn Ala Ile Asp Val Leu
        355
```

<210> SEQ ID NO 10
<211> LENGTH: 359
<212> TYPE: PRT
<213> ORGANISM: Escherichia coli

<400> SEQUENCE: 10

```
Met Ser Lys Ile Phe Asp Phe Val Lys Pro Gly Val Ile Thr Gly Asp
  1               5                  10                  15

Asp Val Gln Lys Val Phe Gln Val Ala Lys Glu Asn Asn Phe Ala Leu
             20                  25                  30

Pro Ala Val Asn Cys Val Gly Thr Asp Ser Ile Asn Ala Val Leu Glu
         35                  40                  45

Thr Ala Ala Lys Val Lys Ala Pro Val Ile Val Gln Phe Ser Asn Gly
     50                  55                  60

Gly Ala Ser Phe Ile Ala Gly Lys Gly Val Lys Ser Asp Val Pro Gln
 65                  70                  75                  80

Gly Ala Ala Ile Leu Gly Ala Ile Ser Gly Ala His His Val His Gln
                 85                  90                  95

Met Ala Glu His Tyr Gly Val Pro Val Ile Leu His Thr Asp His Cys
            100                 105                 110

Ala Lys Lys Leu Leu Pro Trp Ile Asp Gly Leu Leu Asp Ala Gly Glu
        115                 120                 125

Lys His Phe Ala Ala Thr Gly Lys Pro Leu Phe Ser Ser His Met Ile
    130                 135                 140
```

```
Asp Leu Ser Glu Glu Ser Leu Gln Glu Asn Ile Glu Ile Cys Ser Lys
145                 150                 155                 160

Tyr Leu Glu Arg Met Ser Lys Ile Gly Met Thr Leu Glu Ile Glu Leu
            165                 170                 175

Gly Cys Thr Gly Gly Glu Glu Asp Gly Val Asp Asn Ser His Met Asp
        180                 185                 190

Ala Ser Ala Leu Tyr Thr Gln Pro Glu Asp Val Asp Tyr Ala Tyr Thr
    195                 200                 205

Glu Leu Ser Lys Ile Ser Pro Arg Phe Thr Ile Ala Ala Ser Phe Gly
210                 215                 220

Asn Val His Gly Val Tyr Lys Pro Gly Asn Val Val Leu Thr Pro Thr
225                 230                 235                 240

Ile Leu Arg Asp Ser Gln Glu Tyr Val Ser Lys Lys His Asn Leu Pro
                245                 250                 255

His Asn Ser Leu Asn Phe Val Phe His Gly Gly Ser Gly Ser Thr Ala
            260                 265                 270

Gln Glu Ile Lys Asp Ser Val Ser Tyr Gly Val Val Lys Met Asn Ile
        275                 280                 285

Asp Thr Asp Thr Gln Trp Ala Thr Trp Glu Gly Val Leu Asn Tyr Tyr
290                 295                 300

Lys Ala Asn Glu Ala Tyr Leu Gln Gly Gln Leu Gly Asn Pro Lys Gly
305                 310                 315                 320

Glu Asp Gln Pro Asn Lys Lys Tyr Tyr Asp Pro Arg Val Trp Leu Arg
                325                 330                 335

Ala Gly Gln Thr Ser Met Ile Ala Arg Leu Glu Lys Ala Phe Gln Glu
            340                 345                 350

Leu Asn Ala Ile Asp Val Leu
            355

<210> SEQ ID NO 11
<211> LENGTH: 921
<212> TYPE: DNA
<213> ORGANISM: Salmonella typhi
<220> FEATURE:
<221> NAME/KEY: CDS
<222> LOCATION: (1)..(918)

<400> SEQUENCE: 11 atg gat atc gcg gtt att ggc tct aac atg gtg gac ctt atc acc tac      48
Met Asp Ile Ala Val Ile Gly Ser Asn Met Val Asp Leu Ile Thr Tyr
  1               5                  10                  15 acc aac cag atg ccc aaa gaa ggg gaa act ctg gaa gcg ccg gcg ttt      96
Thr Asn Gln Met Pro Lys Glu Gly Glu Thr Leu Glu Ala Pro Ala Phe
             20                  25                  30 aaa atc ggc tgc ggc gga aaa ggg gcg aac cag gcc gtg gcg gcc gct     144
Lys Ile Gly Cys Gly Gly Lys Gly Ala Asn Gln Ala Val Ala Ala Ala
         35                  40                  45 aag ctc aat tca aaa gta ttg atg ttg acc aaa gtg ggc gac gat att     192
Lys Leu Asn Ser Lys Val Leu Met Leu Thr Lys Val Gly Asp Asp Ile
     50                  55                  60 ttt gcc gac aac acc att cgt aat ctc gaa tcc tgg ggg atc aat acg     240
Phe Ala Asp Asn Thr Ile Arg Asn Leu Glu Ser Trp Gly Ile Asn Thr
 65                  70                  75                  80 acg tat gta gaa aaa gta ccg tgt acc agc agc ggc gta gcg ccg att     288
Thr Tyr Val Glu Lys Val Pro Cys Thr Ser Ser Gly Val Ala Pro Ile
                 85                  90                  95 ttc gtc aac gcc aac tcc agc aac agc att ctg atc atc aaa ggc gct     336
Phe Val Asn Ala Asn Ser Ser Asn Ser Ile Leu Ile Ile Lys Gly Ala
            100                 105                 110
```

-continued

```
              100                 105                 110
aac aag ttt ctc tcg ccg gaa gat atc gat cgc gcg gcg gaa gat tta    384
Asn Lys Phe Leu Ser Pro Glu Asp Ile Asp Arg Ala Ala Glu Asp Leu
            115                 120                 125 aaa aaa tgc cag ctt att gtt ctg caa ctg gaa gtt cag ctt gaa acg    432
Lys Lys Cys Gln Leu Ile Val Leu Gln Leu Glu Val Gln Leu Glu Thr
        130                 135                 140 gtt tat cac gca ata gaa ttt ggc aag aaa cac ggg att gaa gtg tta    480
Val Tyr His Ala Ile Glu Phe Gly Lys Lys His Gly Ile Glu Val Leu
145                 150                 155                 160 tta aac cct gcg cca gca tta cgg gaa tta gat atg tct tat gcc tgt    528
Leu Asn Pro Ala Pro Ala Leu Arg Glu Leu Asp Met Ser Tyr Ala Cys
                165                 170                 175 aaa tgc gat ttc ttt gta cct aat gaa acc gag ctg gaa ata tta acc    576
Lys Cys Asp Phe Phe Val Pro Asn Glu Thr Glu Leu Glu Ile Leu Thr
            180                 185                 190 ggt atg cca gtg gat acc tat gac cat att cgc gca gcg gca cgt tcg    624
Gly Met Pro Val Asp Thr Tyr Asp His Ile Arg Ala Ala Ala Arg Ser
        195                 200                 205 ctg gta gat aaa ggg ctg aac aat att att gtc acc atg ggc gag aaa    672
Leu Val Asp Lys Gly Leu Asn Asn Ile Ile Val Thr Met Gly Glu Lys
    210                 215                 220 ggc gcg ctg tgg atg acg cgt gac cag gaa gtc cat gtt ccg gcg ttt    720
Gly Ala Leu Trp Met Thr Arg Asp Gln Glu Val His Val Pro Ala Phe
225                 230                 235                 240 aga gtg aac gct gtt gat acc agc ggc gcg ggc gat gcc ttt atc ggc    768
Arg Val Asn Ala Val Asp Thr Ser Gly Ala Gly Asp Ala Phe Ile Gly
                245                 250                 255 tgt ttc gcg cat tac tac gtc cag agc ggg gat gtg gaa gcc gcc atg    816
Cys Phe Ala His Tyr Tyr Val Gln Ser Gly Asp Val Glu Ala Ala Met
            260                 265                 270 aaa aaa gcc gtc ctc ttt gcc gct ttc agc gtc acc ggg aaa ggc acc    864
Lys Lys Ala Val Leu Phe Ala Ala Phe Ser Val Thr Gly Lys Gly Thr
        275                 280                 285 caa tcc tct tat cca agc att gag caa ttt aat gag tat ctt tcg ttg    912
Gln Ser Ser Tyr Pro Ser Ile Glu Gln Phe Asn Glu Tyr Leu Ser Leu
    290                 295                 300 aac gaa taa                                                         921
Asn Glu
305
```

<210> SEQ ID NO 12
<211> LENGTH: 306
<212> TYPE: PRT
<213> ORGANISM: Salmonella typhi

<400> SEQUENCE: 12

```
Met Asp Ile Ala Val Ile Gly Ser Asn Met Val Asp Leu Ile Thr Tyr
 1               5                  10                  15

Thr Asn Gln Met Pro Lys Glu Gly Glu Thr Leu Glu Ala Pro Ala Phe
                20                  25                  30

Lys Ile Gly Cys Gly Gly Lys Gly Ala Asn Gln Ala Val Ala Ala Ala
            35                  40                  45

Lys Leu Asn Ser Lys Val Leu Met Leu Thr Lys Val Gly Asp Asp Ile
        50                  55                  60

Phe Ala Asp Asn Thr Ile Arg Asn Leu Glu Ser Trp Gly Ile Asn Thr
65                  70                  75                  80

Thr Tyr Val Glu Lys Val Pro Cys Thr Ser Ser Gly Val Ala Pro Ile
                85                  90                  95
```

```
Phe Val Asn Ala Asn Ser Ser Asn Ser Ile Leu Ile Ile Lys Gly Ala
                100                 105                 110

Asn Lys Phe Leu Ser Pro Glu Asp Ile Asp Arg Ala Ala Glu Asp Leu
            115                 120                 125

Lys Lys Cys Gln Leu Ile Val Leu Gln Leu Glu Val Gln Leu Glu Thr
        130                 135                 140

Val Tyr His Ala Ile Glu Phe Gly Lys Lys His Gly Ile Glu Val Leu
145                 150                 155                 160

Leu Asn Pro Ala Pro Ala Leu Arg Glu Leu Asp Met Ser Tyr Ala Cys
                165                 170                 175

Lys Cys Asp Phe Phe Val Pro Asn Glu Thr Glu Leu Glu Ile Leu Thr
            180                 185                 190

Gly Met Pro Val Asp Thr Tyr Asp His Ile Arg Ala Ala Ala Arg Ser
        195                 200                 205

Leu Val Asp Lys Gly Leu Asn Asn Ile Ile Val Thr Met Gly Glu Lys
210                 215                 220

Gly Ala Leu Trp Met Thr Arg Asp Gln Glu Val His Val Pro Ala Phe
225                 230                 235                 240

Arg Val Asn Ala Val Asp Thr Ser Gly Ala Gly Asp Ala Phe Ile Gly
                245                 250                 255

Cys Phe Ala His Tyr Tyr Val Gln Ser Gly Asp Val Glu Ala Ala Met
            260                 265                 270

Lys Lys Ala Val Leu Phe Ala Ala Phe Ser Val Thr Gly Lys Gly Thr
        275                 280                 285

Gln Ser Ser Tyr Pro Ser Ile Glu Gln Phe Asn Glu Tyr Leu Ser Leu
    290                 295                 300

Asn Glu
305

<210> SEQ ID NO 13
<211> LENGTH: 483
<212> TYPE: DNA
<213> ORGANISM: Lactobacillus leichmannii
<220> FEATURE:
<221> NAME/KEY: CDS
<222> LOCATION: (10)..(480)

<400> SEQUENCE: 13 gtatactaa atg cca aaa aag acg atc tac ttc ggt gcc ggc tgg ttc act      51
          Met Pro Lys Lys Thr Ile Tyr Phe Gly Ala Gly Trp Phe Thr
           1               5                  10 gac cgc caa aac aaa gcc tac aag gaa gcc atg gaa gcc ctc aag gaa        99
Asp Arg Gln Asn Lys Ala Tyr Lys Glu Ala Met Glu Ala Leu Lys Glu
 15                  20                  25                  30 aac cca acg att gac ctg gaa aac agc tac gtt ccc ctg gac aac cag       147
Asn Pro Thr Ile Asp Leu Glu Asn Ser Tyr Val Pro Leu Asp Asn Gln
                 35                  40                  45 tac aag ggt atc cgg gtt gat gaa cac ccg gaa tac ctg cat gac aag       195
Tyr Lys Gly Ile Arg Val Asp Glu His Pro Glu Tyr Leu His Asp Lys
             50                  55                  60 gtt tgg gct acg gcc acc tac aac aac gac ttg aac ggg atc aag acc       243
Val Trp Ala Thr Ala Thr Tyr Asn Asn Asp Leu Asn Gly Ile Lys Thr
         65                  70                  75 aac gac atc atg ctg ggt gtc tac atc cct gac gaa gaa gac gtc ggc       291
Asn Asp Ile Met Leu Gly Val Tyr Ile Pro Asp Glu Glu Asp Val Gly
     80                  85                  90 ctg ggc atg gaa ctg ggt tac gcc ttg agc caa ggc aag tac gtc ctt       339
```

-continued

```
Leu Gly Met Glu Leu Gly Tyr Ala Leu Ser Gln Gly Lys Tyr Val Leu
 95                 100                 105                 110 ttg gtc atc ccg gac gaa gac tac ggc aag ccg atc aac ctc atg agc      387
Leu Val Ile Pro Asp Glu Asp Tyr Gly Lys Pro Ile Asn Leu Met Ser
            115                 120                 125 tgg ggc gtc agc gac aac gtg atc aag atg agc cag ctg aag gac ttc      435
Trp Gly Val Ser Asp Asn Val Ile Lys Met Ser Gln Leu Lys Asp Phe
        130                 135                 140 aac ttc aac aag ccg cgc ttc gac ttc tac gaa ggt gcc gta tac taa      483
Asn Phe Asn Lys Pro Arg Phe Asp Phe Tyr Glu Gly Ala Val Tyr
    145                 150                 155
```

<210> SEQ ID NO 14
<211> LENGTH: 157
<212> TYPE: PRT
<213> ORGANISM: Lactobacillus leichmannii

<400> SEQUENCE: 14

```
Met Pro Lys Lys Thr Ile Tyr Phe Gly Ala Gly Trp Phe Thr Asp Arg
  1               5                  10                  15

Gln Asn Lys Ala Tyr Lys Glu Ala Met Glu Ala Leu Lys Glu Asn Pro
                 20                  25                  30

Thr Ile Asp Leu Glu Asn Ser Tyr Val Pro Leu Asp Asn Gln Tyr Lys
             35                  40                  45

Gly Ile Arg Val Asp Glu His Pro Glu Tyr Leu His Asp Lys Val Trp
         50                  55                  60

Ala Thr Ala Thr Tyr Asn Asn Asp Leu Asn Gly Ile Lys Thr Asn Asp
 65                  70                  75                  80

Ile Met Leu Gly Val Tyr Ile Pro Asp Glu Glu Asp Val Gly Leu Gly
                 85                  90                  95

Met Glu Leu Gly Tyr Ala Leu Ser Gln Gly Lys Tyr Val Leu Leu Val
            100                 105                 110

Ile Pro Asp Glu Asp Tyr Gly Lys Pro Ile Asn Leu Met Ser Trp Gly
        115                 120                 125

Val Ser Asp Asn Val Ile Lys Met Ser Gln Leu Lys Asp Phe Asn Phe
    130                 135                 140

Asn Lys Pro Arg Phe Asp Phe Tyr Glu Gly Ala Val Tyr
145                 150                 155
```

<210> SEQ ID NO 15
<211> LENGTH: 720
<212> TYPE: DNA
<213> ORGANISM: Escherichia coli
<220> FEATURE:
<221> NAME/KEY: CDS
<222> LOCATION: (1)..(717)

<400> SEQUENCE: 15

```
atg gct acc cca cac att aat gca gaa atg ggc gat ttc gct gac gta       48
Met Ala Thr Pro His Ile Asn Ala Glu Met Gly Asp Phe Ala Asp Val
  1               5                  10                  15 gtt ttg atg cca ggc gac ccg ctg cgt gcg aag tat att gct gaa act       96
Val Leu Met Pro Gly Asp Pro Leu Arg Ala Lys Tyr Ile Ala Glu Thr
                 20                  25                  30 ttc ctt gaa gat gcc cgt gaa gtg aac aac gtt cgc ggt atg ctg ggc      144
Phe Leu Glu Asp Ala Arg Glu Val Asn Asn Val Arg Gly Met Leu Gly
             35                  40                  45 ttc acc ggt act tac aaa ggc cgc aaa att tcc gta atg ggt cac ggt      192
Phe Thr Gly Thr Tyr Lys Gly Arg Lys Ile Ser Val Met Gly His Gly
         50                  55                  60
```

-continued

```
atg ggt atc ccg tcc tgc tcc atc tac acc aaa gaa ctg atc acc gat       240
Met Gly Ile Pro Ser Cys Ser Ile Tyr Thr Lys Glu Leu Ile Thr Asp
 65                  70                  75                  80 ttc ggc gtg aag aaa att atc cgc gtg ggt tcc tgt ggc gca gtt ctg       288
Phe Gly Val Lys Lys Ile Ile Arg Val Gly Ser Cys Gly Ala Val Leu
                 85                  90                  95 ccg cac gta aaa ctg cgc gac gtc gtt atc ggt atg ggt acc tgc acc       336
Pro His Val Lys Leu Arg Asp Val Val Ile Gly Met Gly Thr Cys Thr
            100                 105                 110 gat tcc aaa gtt aac cgc atc cgt ttt aaa gac cat gac ttt gcc gct       384
Asp Ser Lys Val Asn Arg Ile Arg Phe Lys Asp His Asp Phe Ala Ala
        115                 120                 125 atc gct gac ttc gac atg gtg cgt aac gca gta gat gca gct aaa gca       432
Ile Ala Asp Phe Asp Met Val Arg Asn Ala Val Asp Ala Ala Lys Ala
    130                 135                 140 ctg ggt att gat gct cgc gtg ggt aac ctg ttc tcc gct gac ctg ttc       480
Leu Gly Ile Asp Ala Arg Val Gly Asn Leu Phe Ser Ala Asp Leu Phe
145                 150                 155                 160 tac tct ccg gac ggc gaa atg ttc gac gtg atg gaa aaa tac ggc att       528
Tyr Ser Pro Asp Gly Glu Met Phe Asp Val Met Glu Lys Tyr Gly Ile
                165                 170                 175 ctc ggc gtg gaa atg gaa gcg gct ggt atc tac ggc gtc gct gca gaa       576
Leu Gly Val Glu Met Glu Ala Ala Gly Ile Tyr Gly Val Ala Ala Glu
            180                 185                 190 ttt ggc gcg aaa gcc ctg acc atc tgc acc gta tct gac cac atc cgc       624
Phe Gly Ala Lys Ala Leu Thr Ile Cys Thr Val Ser Asp His Ile Arg
        195                 200                 205 act cac gag cag acc act gcc gct gag cgt cag act acc ttc aac aac       672
Thr His Glu Gln Thr Thr Ala Ala Glu Arg Gln Thr Thr Phe Asn Asn
    210                 215                 220 atg atc aaa atc gca ctg gaa tcc gtt ctg ctg ggc gat aaa gag taa       720
Met Ile Lys Ile Ala Leu Glu Ser Val Leu Leu Gly Asp Lys Glu
225                 230                 235
```

<210> SEQ ID NO 16
<211> LENGTH: 239
<212> TYPE: PRT
<213> ORGANISM: Escherichia coli

<400> SEQUENCE: 16

```
Met Ala Thr Pro His Ile Asn Ala Glu Met Gly Asp Phe Ala Asp Val
  1               5                  10                  15

Val Leu Met Pro Gly Asp Pro Leu Arg Ala Lys Tyr Ile Ala Glu Thr
             20                  25                  30

Phe Leu Glu Asp Ala Arg Glu Val Asn Asn Val Arg Gly Met Leu Gly
         35                  40                  45

Phe Thr Gly Thr Tyr Lys Gly Arg Lys Ile Ser Val Met Gly His Gly
     50                  55                  60

Met Gly Ile Pro Ser Cys Ser Ile Tyr Thr Lys Glu Leu Ile Thr Asp
 65                  70                  75                  80

Phe Gly Val Lys Lys Ile Ile Arg Val Gly Ser Cys Gly Ala Val Leu
                 85                  90                  95

Pro His Val Lys Leu Arg Asp Val Val Ile Gly Met Gly Thr Cys Thr
            100                 105                 110

Asp Ser Lys Val Asn Arg Ile Arg Phe Lys Asp His Asp Phe Ala Ala
        115                 120                 125

Ile Ala Asp Phe Asp Met Val Arg Asn Ala Val Asp Ala Ala Lys Ala
    130                 135                 140
```

```
Leu Gly Ile Asp Ala Arg Val Gly Asn Leu Phe Ser Ala Asp Leu Phe
145                 150                 155                 160

Tyr Ser Pro Asp Gly Glu Met Phe Asp Val Met Glu Lys Tyr Gly Ile
            165                 170                 175

Leu Gly Val Glu Met Glu Ala Ala Gly Ile Tyr Gly Val Ala Ala Glu
            180                 185                 190

Phe Gly Ala Lys Ala Leu Thr Ile Cys Thr Val Ser Asp His Ile Arg
            195                 200                 205

Thr His Glu Gln Thr Thr Ala Ala Glu Arg Gln Thr Thr Phe Asn Asn
            210                 215                 220

Met Ile Lys Ile Ala Leu Glu Ser Val Leu Leu Gly Asp Lys Glu
225                 230                 235

<210> SEQ ID NO 17
<211> LENGTH: 1224
<212> TYPE: DNA
<213> ORGANISM: Escherichia coli
<220> FEATURE:
<221> NAME/KEY: CDS
<222> LOCATION: (1)..(1221)

<400> SEQUENCE: 17 atg aaa cgt gca ttt att atg gtg ctg gac tca ttc ggc atc ggc gct    48
Met Lys Arg Ala Phe Ile Met Val Leu Asp Ser Phe Gly Ile Gly Ala
 1               5                  10                  15 aca gaa gat gca gaa cgc ttt ggt gac gtc ggg gct gac acc ctg ggt    96
Thr Glu Asp Ala Glu Arg Phe Gly Asp Val Gly Ala Asp Thr Leu Gly
                20                  25                  30 cat atc gca gaa gct tgt gcc aaa ggc gaa gct gat aac ggt cgt aaa   144
His Ile Ala Glu Ala Cys Ala Lys Gly Glu Ala Asp Asn Gly Arg Lys
            35                  40                  45 ggc ccg ctc aat ctg cca aat ctg acc cgt ctg ggg ctg gcg aaa gca   192
Gly Pro Leu Asn Leu Pro Asn Leu Thr Arg Leu Gly Leu Ala Lys Ala
        50                  55                  60 cac gaa ggt tct acc ggt ttc att ccg gcg gga atg gac ggc aac gct   240
His Glu Gly Ser Thr Gly Phe Ile Pro Ala Gly Met Asp Gly Asn Ala
 65                  70                  75                  80 gaa gtt atc ggc gcg tac gca tgg gcg cac gaa atg tca tcc ggt aaa   288
Glu Val Ile Gly Ala Tyr Ala Trp Ala His Glu Met Ser Ser Gly Lys
                 85                  90                  95 gat acc ccg tct ggt cac tgg gaa att gcc ggc gtc ccg gtt ctg ttt   336
Asp Thr Pro Ser Gly His Trp Glu Ile Ala Gly Val Pro Val Leu Phe
            100                 105                 110 gag tgg gga tat ttc tcc gat cac gaa aac agc ttc ccg caa gag ctg   384
Glu Trp Gly Tyr Phe Ser Asp His Glu Asn Ser Phe Pro Gln Glu Leu
        115                 120                 125 ctg gat aaa ctg gtc gaa cgc gct aat ctg ccg ggt tac ctc ggt aac   432
Leu Asp Lys Leu Val Glu Arg Ala Asn Leu Pro Gly Tyr Leu Gly Asn
130                 135                 140 tgc cac tct tcc ggt acg gtc att ctg gat caa ctg ggc gaa gag cac   480
Cys His Ser Ser Gly Thr Val Ile Leu Asp Gln Leu Gly Glu Glu His
145                 150                 155                 160 atg aaa acc ggc aag ccg att ttc tat acc tcc gct gac tcc gtg ttc   528
Met Lys Thr Gly Lys Pro Ile Phe Tyr Thr Ser Ala Asp Ser Val Phe
                165                 170                 175 cag att gcc tgc cat gaa gaa act ttc ggt ctg gat aaa ctc tac gaa   576
Gln Ile Ala Cys His Glu Glu Thr Phe Gly Leu Asp Lys Leu Tyr Glu
            180                 185                 190 ctg tgc gaa atc gcc cgt gaa gag ctg acc aac ggc ggc tac aat atc   624
```

```

Leu Cys Glu Ile Ala Arg Glu Leu Thr Asn Gly Gly Tyr Asn Ile
        195                 200                 205 ggt cgt gtt atc gct cgt ccg ttt atc ggc gac aaa gcc ggt aac ttc        672
Gly Arg Val Ile Ala Arg Pro Phe Ile Gly Asp Lys Ala Gly Asn Phe
    210                 215                 220 caa cgt acc ggt aac cgt cac gac ctg gct gtt gag ccg cca gca ccg        720
Gln Arg Thr Gly Asn Arg His Asp Leu Ala Val Glu Pro Pro Ala Pro
225                 230                 235                 240 acc gtg ctg cag aaa ctg gtt gat gaa aaa cac ggc cag gtg gtt tct        768
Thr Val Leu Gln Lys Leu Val Asp Glu Lys His Gly Gln Val Val Ser
                245                 250                 255 gtc ggt aaa att gcg gac atc tac gcc aac tgc ggt atc acc aaa aaa        816
Val Gly Lys Ile Ala Asp Ile Tyr Ala Asn Cys Gly Ile Thr Lys Lys
            260                 265                 270 gtg aaa gcg act ggc ctg gac gcg ctg ttt gac acc acc atc aaa gag        864
Val Lys Ala Thr Gly Leu Asp Ala Leu Phe Asp Thr Thr Ile Lys Glu
        275                 280                 285 atg aaa gaa gcg ggt gat aac acc atc gtc ttc acc aac ttc gtt gac        912
Met Lys Glu Ala Gly Asp Asn Thr Ile Val Phe Thr Asn Phe Val Asp
    290                 295                 300 ttc gac tct tcc tgg ggc cac cgt cgc gac gtc gcc ggt tat gcc gcg        960
Phe Asp Ser Ser Trp Gly His Arg Arg Asp Val Ala Gly Tyr Ala Ala
305                 310                 315                 320 ggt ctg gaa ctg ttc gac cgc cgt ctg ccg gag ctg atg tct ctg ctg       1008
Gly Leu Glu Leu Phe Asp Arg Arg Leu Pro Glu Leu Met Ser Leu Leu
                325                 330                 335 cgc gat gac gac atc ctg atc ctc acc gct gac cac ggt tgc gat ccg       1056
Arg Asp Asp Asp Ile Leu Ile Leu Thr Ala Asp His Gly Cys Asp Pro
            340                 345                 350 acc tgg acc ggt act gac cac acg cgt gaa cac att ccg gta ctg gta       1104
Thr Trp Thr Gly Thr Asp His Thr Arg Glu His Ile Pro Val Leu Val
        355                 360                 365 tat ggc ccg aaa gta aaa ccg ggc tca ctg ggt cat cgt gaa acc ttc       1152
Tyr Gly Pro Lys Val Lys Pro Gly Ser Leu Gly His Arg Glu Thr Phe
    370                 375                 380 gcg gat atc ggc cag act ctg gca aaa tat ttt ggt act tct gat atg       1200
Ala Asp Ile Gly Gln Thr Leu Ala Lys Tyr Phe Gly Thr Ser Asp Met
385                 390                 395                 400 gaa tat ggc aaa gcc atg ttc tga                                       1224
Glu Tyr Gly Lys Ala Met Phe
                405

<210> SEQ ID NO 18
<211> LENGTH: 407
<212> TYPE: PRT
<213> ORGANISM: Escherichia coli

<400> SEQUENCE: 18

Met Lys Arg Ala Phe Ile Met Val Leu Asp Ser Phe Gly Ile Gly Ala
1               5                   10                  15

Thr Glu Asp Ala Glu Arg Phe Gly Asp Val Gly Ala Asp Thr Leu Gly
                20                  25                  30

His Ile Ala Glu Ala Cys Ala Lys Gly Glu Ala Asp Asn Gly Arg Lys
            35                  40                  45

Gly Pro Leu Asn Leu Pro Asn Leu Thr Arg Leu Gly Leu Ala Lys Ala
        50                  55                  60

His Glu Gly Ser Thr Gly Phe Ile Pro Ala Gly Met Asp Gly Asn Ala
65                  70                  75                  80

Glu Val Ile Gly Ala Tyr Ala Trp Ala His Glu Met Ser Ser Gly Lys
```

```
                      85                  90                  95
Asp Thr Pro Ser Gly His Trp Glu Ile Ala Gly Val Pro Val Leu Phe
            100                 105                 110
Glu Trp Gly Tyr Phe Ser Asp His Glu Asn Ser Phe Pro Gln Glu Leu
        115                 120                 125
Leu Asp Lys Leu Val Glu Arg Ala Asn Leu Pro Gly Tyr Leu Gly Asn
    130                 135                 140
Cys His Ser Ser Gly Thr Val Ile Leu Asp Gln Leu Gly Glu Glu His
145                 150                 155                 160
Met Lys Thr Gly Lys Pro Ile Phe Tyr Thr Ser Ala Asp Ser Val Phe
                165                 170                 175
Gln Ile Ala Cys His Glu Glu Thr Phe Gly Leu Asp Lys Leu Tyr Glu
            180                 185                 190
Leu Cys Glu Ile Ala Arg Glu Glu Leu Thr Asn Gly Gly Tyr Asn Ile
        195                 200                 205
Gly Arg Val Ile Ala Arg Pro Phe Ile Gly Asp Lys Ala Gly Asn Phe
    210                 215                 220
Gln Arg Thr Gly Asn Arg His Asp Leu Ala Val Glu Pro Pro Ala Pro
225                 230                 235                 240
Thr Val Leu Gln Lys Leu Val Asp Glu Lys His Gly Gln Val Val Ser
                245                 250                 255
Val Gly Lys Ile Ala Asp Ile Tyr Ala Asn Cys Gly Ile Thr Lys Lys
            260                 265                 270
Val Lys Ala Thr Gly Leu Asp Ala Leu Phe Asp Thr Thr Ile Lys Glu
        275                 280                 285
Met Lys Glu Ala Gly Asp Asn Thr Ile Val Phe Thr Asn Phe Val Asp
    290                 295                 300
Phe Asp Ser Ser Trp Gly His Arg Arg Asp Val Ala Gly Tyr Ala Ala
305                 310                 315                 320
Gly Leu Glu Leu Phe Asp Arg Arg Leu Pro Glu Leu Met Ser Leu Leu
                325                 330                 335
Arg Asp Asp Asp Ile Leu Ile Leu Thr Ala Asp His Gly Cys Asp Pro
            340                 345                 350
Thr Trp Thr Gly Thr Asp His Thr Arg Glu His Ile Pro Val Leu Val
        355                 360                 365
Tyr Gly Pro Lys Val Lys Pro Gly Ser Leu Gly His Arg Glu Thr Phe
    370                 375                 380
Ala Asp Ile Gly Gln Thr Leu Ala Lys Tyr Phe Gly Thr Ser Asp Met
385                 390                 395                 400
Glu Tyr Gly Lys Ala Met Phe
                405

<210> SEQ ID NO 19
<211> LENGTH: 780
<212> TYPE: DNA
<213> ORGANISM: Escherichia coli
<220> FEATURE:
<221> NAME/KEY: CDS
<222> LOCATION: (1)..(777)

<400> SEQUENCE: 19 atg act gat ctg aaa gca agc agc ctg cgt gca ctg aaa ttg atg gac    48
Met Thr Asp Leu Lys Ala Ser Ser Leu Arg Ala Leu Lys Leu Met Asp
 1               5                  10                  15 ctg aac acc ctg aat gac gac gac acc gac gag aaa gtg atc gcc ctg    96
Leu Asn Thr Leu Asn Asp Asp Asp Thr Asp Glu Lys Val Ile Ala Leu
```

```
                     20                  25                  30
tgt cat cag gcc aaa act ccg gtc ggc aat acc gcc gct atc tgt atc    144
Cys His Gln Ala Lys Thr Pro Val Gly Asn Thr Ala Ala Ile Cys Ile
         35                  40                  45 tat cct cgc ttt atc ccg att gct cgc aaa act ctg aaa gag cag ggc    192
Tyr Pro Arg Phe Ile Pro Ile Ala Arg Lys Thr Leu Lys Glu Gln Gly
     50                  55                  60 acc ccg gaa atc cgt atc gct acg gta acc aac ttc cca cac ggt aac    240
Thr Pro Glu Ile Arg Ile Ala Thr Val Thr Asn Phe Pro His Gly Asn
 65                  70                  75                  80 gac gac atc gac atc gcg ctg gca gaa acc cgt gcg gca atc gcc tac    288
Asp Asp Ile Asp Ile Ala Leu Ala Glu Thr Arg Ala Ala Ile Ala Tyr
                 85                  90                  95 ggt gct gat gaa gtt gac gtt gtg ttc ccg tac cgc gcg ctg atg gcg    336
Gly Ala Asp Glu Val Asp Val Val Phe Pro Tyr Arg Ala Leu Met Ala
            100                 105                 110 ggt aac gag cag gtt ggt ttt gac ctg gtg aaa gcc tgt aaa gag gct    384
Gly Asn Glu Gln Val Gly Phe Asp Leu Val Lys Ala Cys Lys Glu Ala
        115                 120                 125 tgc gcg gca gcg aat gta ctg ctg aaa gtg atc atc gaa acc ggc gaa    432
Cys Ala Ala Ala Asn Val Leu Leu Lys Val Ile Ile Glu Thr Gly Glu
    130                 135                 140 ctg aaa gac gaa gcg ctg atc cgt aaa gcg tct gaa atc tcc atc aaa    480
Leu Lys Asp Glu Ala Leu Ile Arg Lys Ala Ser Glu Ile Ser Ile Lys
145                 150                 155                 160 gcg ggt gtg gac ttc atc aaa acc tct acc ggt aaa gtg gct gtg aac    528
Ala Gly Val Asp Phe Ile Lys Thr Ser Thr Gly Lys Val Ala Val Asn
                165                 170                 175 gcg acg ccg gaa agc gcg cgt atc atg atg gaa gtg atc cgt gat atg    576
Ala Thr Pro Glu Ser Ala Arg Ile Met Met Glu Val Ile Arg Asp Met
            180                 185                 190 ggc gta gaa aaa acc gtt ggt ttc aaa ccg gcg ggc ggc gtg cgt act    624
Gly Val Glu Lys Thr Val Gly Phe Lys Pro Ala Gly Gly Val Arg Thr
        195                 200                 205 gcg gaa gat gcg cag aaa tat ctc gcc att gca gat gaa ctg ttc ggt    672
Ala Glu Asp Ala Gln Lys Tyr Leu Ala Ile Ala Asp Glu Leu Phe Gly
    210                 215                 220 gct gac tgg gca gat gcg cgt cac tac cgc ttt ggc gct tcc agc ctg    720
Ala Asp Trp Ala Asp Ala Arg His Tyr Arg Phe Gly Ala Ser Ser Leu
225                 230                 235                 240 ctg gca agc ctg ctg aaa gcg ctg ggt cac ggc gac ggt aag agc gcc    768
Leu Ala Ser Leu Leu Lys Ala Leu Gly His Gly Asp Gly Lys Ser Ala
                245                 250                 255 agc agc tac taa                                                    780
Ser Ser Tyr <210> SEQ ID NO 20
<211> LENGTH: 259
<212> TYPE: PRT
<213> ORGANISM: Escherichia coli

<400> SEQUENCE: 20

Met Thr Asp Leu Lys Ala Ser Ser Leu Arg Ala Leu Lys Leu Met Asp
 1               5                  10                  15

Leu Asn Thr Leu Asn Asp Asp Thr Asp Glu Lys Val Ile Ala Leu
             20                  25                  30

Cys His Gln Ala Lys Thr Pro Val Gly Asn Thr Ala Ala Ile Cys Ile
         35                  40                  45

Tyr Pro Arg Phe Ile Pro Ile Ala Arg Lys Thr Leu Lys Glu Gln Gly
```

-continued

```
            50                  55                  60
Thr Pro Glu Ile Arg Ile Ala Thr Val Thr Asn Phe Pro His Gly Asn
65                  70                  75                  80

Asp Asp Ile Asp Ile Ala Leu Ala Glu Thr Arg Ala Ala Ile Ala Tyr
                85                  90                  95

Gly Ala Asp Glu Val Asp Val Val Phe Pro Tyr Arg Ala Leu Met Ala
                100                 105                 110

Gly Asn Glu Gln Val Gly Phe Asp Leu Val Lys Ala Cys Lys Glu Ala
                115                 120                 125

Cys Ala Ala Asn Val Leu Leu Lys Val Ile Ile Glu Thr Gly Glu
130                 135                 140

Leu Lys Asp Glu Ala Leu Ile Arg Lys Ala Ser Glu Ile Ser Ile Lys
145                 150                 155                 160

Ala Gly Val Asp Phe Ile Lys Thr Ser Thr Gly Lys Val Ala Val Asn
                165                 170                 175

Ala Thr Pro Glu Ser Ala Arg Ile Met Met Glu Val Ile Arg Asp Met
                180                 185                 190

Gly Val Glu Lys Thr Val Gly Phe Lys Pro Ala Gly Gly Val Arg Thr
                195                 200                 205

Ala Glu Asp Ala Gln Lys Tyr Leu Ala Ile Ala Asp Glu Leu Phe Gly
                210                 215                 220

Ala Asp Trp Ala Asp Ala Arg His Tyr Arg Phe Gly Ala Ser Ser Leu
225                 230                 235                 240

Leu Ala Ser Leu Leu Lys Ala Leu Gly His Gly Asp Gly Lys Ser Ala
                245                 250                 255

Ser Ser Tyr
```